(12) United States Patent
Lee et al.

(10) Patent No.: US 10,172,553 B2
(45) Date of Patent: Jan. 8, 2019

(54) CONDUCTIVE TEXTILE-BASED INDUCTANCE-TYPE ELECTRODE APPARATUS FOR BIO-SIGNAL DETECTION

(71) Applicants: Industry-Academic Cooperation Foundation, Yonsei University, Seoul (KR); Konkuk University Industrial Cooperation Corp., Seoul (KR)

(72) Inventors: Joo Hyeon Lee, Seoul (KR); Jeong-Whan Lee, Gyeonggi-do (KR); Young-Jae Lee, Gyeonggi-do (KR); Sunok Gi, Busan (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 1080 days.

(21) Appl. No.: 14/471,705

(22) Filed: Aug. 28, 2014

(65) Prior Publication Data

US 2015/0065841 A1 Mar. 5, 2015

(30) Foreign Application Priority Data

Aug. 30, 2013 (KR) ........................ 10-2013-0103990

(51) Int. Cl.
*A61B 5/00* (2006.01)
*A61B 5/053* (2006.01)
(Continued)

(52) U.S. Cl.
CPC .......... *A61B 5/6804* (2013.01); *A61B 5/0245* (2013.01); *A61B 5/0416* (2013.01); *A61B 5/0478* (2013.01); *A61B 5/0492* (2013.01); *A61B 5/053* (2013.01); *A61B 5/4869* (2013.01); *A61B 5/02438* (2013.01); *A61B 5/11* (2013.01);
(Continued)

(58) Field of Classification Search
CPC ... A61B 5/02; A61B 5/04405; A61B 5/04007; A61B 5/04008; A61B 5/05
See application file for complete search history.

(56) References Cited

U.S. PATENT DOCUMENTS

| | | | |
|---|---|---|---|
| 8,428,683 B2 * | 4/2013 | Yoo ...................... | A61B 5/0006 600/301 |
| 2008/0218180 A1 * | 9/2008 | Waffenschmidt ...... | A61B 5/053 324/633 |

(Continued)

FOREIGN PATENT DOCUMENTS

| KR | 1020090084358 | 8/2009 |
|---|---|---|
| KR | 101302600 | 8/2013 |

*Primary Examiner* — Eunhwa Kim
(74) *Attorney, Agent, or Firm* — Duane Morris LLP; Gregory M. Lefkowitz; Jason M. Nolan

(57) ABSTRACT

Provided is a conductive textile-based inductance-type electrode apparatus for bio-signal detection, which includes an electrode unit (10) having a textile electrode (200) for receiving an oscillation signal from an oscillating unit and outputting a bio signal of a subject person, the textile electrode having a spiral coil (101) disposed at a textile sheet (103) formed by spirally turning a coil thread with conductivity from one end to the other end disposed at a center portion thereof, a bottom textile sheet (120) coming in contact with a skin of the subject person, and a buffering member (145) disposed between the electrode unit (10) and the bottom textile sheet (120) to separate the electrode unit (10) from the skin.

13 Claims, 20 Drawing Sheets

(51) Int. Cl.
*A61B 5/0245* (2006.01)
*A61B 5/0416* (2006.01)
*A61B 5/0478* (2006.01)
*A61B 5/0492* (2006.01)
*A61B 5/024* (2006.01)
*A61B 5/11* (2006.01)

(52) U.S. Cl.
CPC . *A61B 2562/0209* (2013.01); *A61B 2562/043* (2013.01); *A61B 2562/125* (2013.01)

(56) References Cited

U.S. PATENT DOCUMENTS

| | | | | |
|---|---|---|---|---|
| 2009/0309579 | A1* | 12/2009 | Cochran | A61B 5/1126 324/207.16 |
| 2010/0113910 | A1* | 5/2010 | Brauers | A61B 5/04085 600/382 |
| 2010/0191090 | A1* | 7/2010 | Shin | A61B 5/0205 600/388 |
| 2010/0222696 | A1* | 9/2010 | Feldkamp | A61B 5/0522 600/547 |
| 2011/0257491 | A1* | 10/2011 | Robertson | A61B 5/0031 600/302 |
| 2013/0085545 | A1* | 4/2013 | Mashiach | A61N 1/0551 607/42 |
| 2014/0206976 | A1* | 7/2014 | Thompson | A61B 5/0006 600/391 |

\* cited by examiner (a)

(b)

CONDUCTIVE TEXTILE-BASED INDUCTANCE-TYPE ELECTRODE APPARATUS FOR BIO-SIGNAL DETECTION

CROSS-REFERENCE TO RELATED APPLICATIONS

This application claims priority under 35 U.S.C. § 119 to Korean Patent Application No. 10-2013-0103990 filed on Aug. 30, 2013 in the Korean Intellectual Property Office, the disclosure of which is incorporated herein by reference in its entirety.

TECHNICAL FIELD

The following disclosure relates to a conductive textile-based inductance-type electrode apparatus for bio-signal detection, in which conductive thread-based or conductive textile-based coil-type magnetic field sensors for detecting a volume change of a living tissue by using an inductance variation are located in a planar or three-dimensional structure on a textile to form an inductance-type bio-signal textile electrode, in which buffering members are located between the inductance-type bio-signal textile electrode and the skin and provided to form a predetermined space so as to reduce a motion artefact, in which the inductance-type bio-signal measurement electrode is configured as a single electrode or an array-type electrode, and in which a textile-based connector for connecting a power to the inductance-type bio-signal textile electrode is provided.

BACKGROUND

Generally, in order to detect electrocardiogram (ECG) or heartbeats, an electrode should be directly bright into contact with the skin, which is inconvenient in various ways. For this reason, various kinds of non-contact electrodes have been developed.

As an existing technique, Korean Patent Registration No. 10-0948941 discloses an apparatus and method for measuring an impedance change of a wrist portion caused by a heartbeat by using an electrode having inductance, which includes a measuring unit for generating an oscillation signal, generating a composite oscillation signal by sensing a change of an external electric and magnetic field, differentiating the measured electric and magnetic field signal to generate a differential signal, and generating a detection signal according to a breath and heartbeat wavelength condition of body, and a signal processing unit for receiving the detection signal output from the measuring unit and extracting a heartbeat signal. This technique has a distinctive feature in the measuring unit and the signal processing unit when an inductive electrode is applied to measure a heartbeat, and a magnetic field is generated as the electrode receives the oscillation signal. In addition, when the electrode generates a composite oscillation signal combined with a bio signal, the state of the electrode is important, for example an adhesion state of the electrode to a human body. In Korean Patent Registration No. 10-0948941, it is impossible to precisely detect a change of a bio signal.

For this, the inventors of this application also have a patent with Korean Patent Registration No. 10-1302000, disclosing an electrode for an inductance-type bio-signal sensor in which a conductive thread-based or conductive textile-based coil-type magnetic field sensor forms a circular spiral coil or a rectangular spiral coil between two textiles and an anti-contact unit made of an insulation material is provided between the coil threads (for example, an insulating thread is stitched).

FIG. 1 is a diagram for illustrating a configuration for detecting a volume change by using a change of inductance by using the conductive textile-based inductance-type bio-signal measurement sensor disclosed in Korean Patent Registration No. 10-1302600.

An inductance-type bio-signal measurement sensor 10 is mounted, and a signal detector 30 is mounted to an outer side of the inductance-type bio-signal measurement sensor. The detector includes an oscillating unit 50 and a demodulating unit 70.

The oscillating unit 50 is composed of an oscillation circuit having L and C to transmit a vibration signal to the inductance-type bio-signal measurement sensor 10.

The inductance-type bio-signal measurement sensor 10 is configured to maximize sensitivity by disposing a ferromagnetic substance core capable of focusing a magnetic flux on a center portion of the coil. In other words, a volume of interest (VOI) 20 may cause a temporal variation, formed by a geometric structure of a coil sensor, namely influenced by a magnetic force, and the conductive textile-based inductance-type bio-signal measurement sensor 10 senses a change of eddy current caused by electric conductivity of a substance located in the volume.

If the inductance-type bio-signal measurement sensor 10 receives a vibration signal, a magnetic field of a time-varying function is formed in a living body in the volume of interest (VOI) 20, and the generated magnetic field creates an eddy current in the substance. The inductance of the sensor is influenced by a movement of a detection target. Therefore, a vibration signal of the heart muscle causes a change of inductance of the coil, and this signal is transmitted through the oscillating unit 50 to the demodulating unit 70.

In detail, a magnetic field is formed by a current minutely flowing on the coil of the inductance-type bio-signal measurement sensor 10. The magnetic field varying according to time induces an eddy current in a detection target (or, in a human body), and the formed induced current generates a minute magnetic field in a direction opposite to the magnetic field formed at the coil. The change of the magnetic field of the coil of the inductance-type bio-signal measurement sensor 10 results in a variation of the inductance (the induced magnetic field) of the coil. To detect the variation, the oscillating unit 50 serving as an oscillation circuit is provided to regard the coil of the inductance-type bio-signal measurement sensor 10 as an inductor circuit, and in this case, a frequency modulation representing a variation of a frequency of an oscillator is exhibited due to a movement of a detection target (in a human body). As one of detection methods, the demodulating unit 70 may trace a modulated frequency by using a phase-locked loop (PLL). If this frequency demodulation is used, a movement of the detection target is exhibited as a PLL output, which allows a movement of the heart to be measured.

Generally, in the bio-signal detection, a bio signal is rarely detected with a single electrode, and two or more electrodes including a reference electrode and a signal electrode are used to detect a bio signal. Therefore, a dual electrode or an array electrode is desired. If a plurality of electrodes is provided like this case, a signal to be detected may be induced to another electrode and thus detected erroneously. Therefore, the electrode structure is very important.

In addition, for allowing a bio signal to be measured during activity, a flexible electrode is demanded.

Moreover, a conductive textile-based inductance-type electrode apparatus for bio-signal detection which has a switch for turning on or off an array electrode is also demanded.

SUMMARY

An embodiment of the present disclosure is directed to providing a conductive textile-based inductance-type electrode apparatus for bio-signal detection, in which a coil-type magnetic field sensor is located in a planar or three-dimensional structure on a textile to form an inductance-type bio-signal textile electrode, buffering members are located between the inductance-type bio-signal textile electrode and the skin, and the buffering members are provided to form a predetermined space, thereby reducing a motion artefact.

Another embodiment of the present disclosure is directed to providing a conductive textile-based inductance-type electrode apparatus for bio-signal detection, in which conductive thread-based or conductive textile-based coil-type magnetic field sensors for detecting a volume change of a living tissue by using an inductance variation are located in a planar or three-dimensional structure on a textile, thereby allowing a bio signal to detected more easily, more conveniently and more accurately.

Another embodiment of the present disclosure is directed to providing a flexible conductive textile-based inductance-type electrode apparatus for bio-signal detection, in which inductance-type bio-signal measurement electrodes are located in a planar or three-dimensional structure on a textile.

Another embodiment of the present disclosure is directed to providing a flexible conductive textile-based inductance-type electrode apparatus for bio-signal detection, which includes an inductance-type bio-signal textile electrode and a textile-based connector for connecting a power to the inductance-type bio-signal textile electrode.

Another embodiment of the present disclosure is directed to providing a flexible conductive textile-based inductance-type electrode apparatus for bio-signal detection, in which an interval is formed between the surface of a cloth in contact with the skin, or the surface of the conductive textile-based inductance-type electrode apparatus for bio-signal detection, and an electrode unit by means of a buffering member so as to have a three-dimensional structure in which the inductance-type bio-signal textile electrode does not easily move in spite of a movement of a subject person, thereby reducing an influence of a motion artefact.

In an aspect of the present disclosure, there is provided a conductive textile-based inductance-type electrode apparatus for bio-signal detection, which includes: an electrode unit having a textile electrode for receiving an oscillation signal from an oscillating unit and outputting a bio signal of a subject person, the textile electrode having a spiral coil disposed at a textile sheet and formed by spirally rotating a coil thread with conductivity from one end to the other end disposed at a center portion thereof; a bottom textile sheet coming in contact with a skin of the subject person; and a buffering member disposed between the electrode unit and the bottom textile sheet to separate the electrode unit from the skin.

In addition, in the conductive textile-based inductance-type electrode apparatus for bio-signal detection according to an embodiment of the present disclosure, the spiral coil forms a loop.

In addition, in the conductive textile-based inductance-type electrode apparatus for bio-signal detection according to an embodiment of the present disclosure, the spiral coil has a doughnut-type hole formed at the center portion.

In addition, in the conductive textile-based inductance-type electrode apparatus for bio-signal detection according to an embodiment of the present disclosure, the electrode unit may further include an anti-contact unit disposed between the coil thread and a coil thread adjacent thereto to prevent the adjacent coil threads from coming into contact with each other.

In addition, in the conductive textile-based inductance-type electrode apparatus for bio-signal detection according to an embodiment of the present disclosure, the anti-contact unit may be formed by coating the coil thread with an insulation material, stitching the textile sheet with a thread with conductivity, embossing the textile sheet, or printing or adhering a material with insulation to a space between the coil threads.

In addition, in the conductive textile-based inductance-type electrode apparatus for bio-signal detection according to an embodiment of the present disclosure, the spiral coil may be formed by embroidering, weaving or knitting a conductive yarn, adhering a conductive material to the textile sheet, or printing a conductive material to the textile sheet.

In addition, in the conductive textile-based inductance-type electrode apparatus for bio-signal detection according to an embodiment of the present disclosure, the textile sheet and the bottom textile sheet may have flexibility to bend corresponding to the skin which moves or bends.

In addition, in the conductive textile-based inductance-type electrode apparatus for bio-signal detection according to an embodiment of the present disclosure, the textile sheet may be formed in a concavely depressed dome shape, and the buffering member may be disposed along a rim of the textile sheet.

In addition, in the conductive textile-based inductance-type electrode apparatus for bio-signal detection according to an embodiment of the present disclosure, the buffering member may extend along the rim of the textile sheet and be integrally formed with the textile sheet.

In addition, in the conductive textile-based inductance-type electrode apparatus for bio-signal detection according to an embodiment of the present disclosure, the bottom textile sheet is a fabric which forms cloth of the subject person.

In addition, in the conductive textile-based inductance-type electrode apparatus for bio-signal detection according to an embodiment of the present disclosure, a plurality of buffering members may be provided to be spaced apart from each other to form a space.

In addition, in the conductive textile-based inductance-type electrode apparatus for bio-signal detection according to an embodiment of the present disclosure, the buffering member is formed by laminating a plurality of sub members with each other.

In addition, the conductive textile-based inductance-type electrode apparatus for bio-signal detection according to an embodiment of the present disclosure may further include a connector unit for electrically connecting one end and the other end of the spiral coil to the oscillating unit or the signal processing unit so that the bio signal is received by a signal processing unit.

In addition, in the conductive textile-based inductance-type electrode apparatus for bio-signal detection according to an embodiment of the present disclosure, the connector unit may include: a textile electrode coupling unit disposed at the textile electrode; and a detector coupling unit disposed at the oscillating unit or the signal processing unit and coupled to the textile electrode coupling unit.

In addition, in the conductive textile-based inductance-type electrode apparatus for bio-signal detection according to an embodiment of the present disclosure, the connector unit may have conductivity and be formed with at least one of a snap button, a buckle, a button, a clip, a hook, a Velcro, a zipper, a cord and a stitch, so that the electrode unit is detachably connected to the oscillating unit or the signal processing unit.

In addition, in the conductive textile-based inductance-type electrode apparatus for bio-signal detection according to an embodiment of the present disclosure, a plurality of electrode units may be provided and laminated with each other.

In addition, in the conductive textile-based inductance-type electrode apparatus for bio-signal detection according to an embodiment of the present disclosure, the electrode unit may include the textile electrode disposed at electrode-mounted textile sheet.

In addition, in the conductive textile-based inductance-type electrode apparatus for bio-signal detection according to an embodiment of the present disclosure, an insulating member may be inserted between the electrode unit and an electrode unit adjacent thereto.

In addition, in the conductive textile-based inductance-type electrode apparatus for bio-signal detection according to an embodiment of the present disclosure, among the spiral coils adjacent to each other, one end of the spiral coil close to the skin may be connected to the other end of the spiral coil far from the skin.

In addition, in the conductive textile-based inductance-type electrode apparatus for bio-signal detection according to an embodiment of the present disclosure, a plurality of electrode units may be provided, turning directions of the spiral coils may be identical to or different from each other, the other end of any one spiral coil may be connected the other end of another spiral coil, and the oscillation signal may be input between one end of any one spiral coil and one end of another spiral coil.

In addition, in the conductive textile-based inductance-type electrode apparatus for bio-signal detection according to an embodiment of the present disclosure, the oscillation signal may be input between the other end of the spiral coil closest to the skin and one end of the spiral coil farthest from the skin.

In addition, in the conductive textile-based inductance-type electrode apparatus for bio-signal detection according to an embodiment of the present disclosure, a plurality of electrode units may be disposed at an electrode-mounted textile sheet to be spaced from each other, and the buffering member may be disposed between the electrode-mounted textile sheet and the bottom textile sheet to correspond to each of the electrode units.

In addition, in the conductive textile-based inductance-type electrode apparatus for bio-signal detection according to an embodiment of the present disclosure, the electrode-mounted textile sheet and the bottom textile sheet are sewed or adhered to each other between adjacent electrode units.

In addition, in the conductive textile-based inductance-type electrode apparatus for bio-signal detection according to an embodiment of the present disclosure, the oscillation signal may be input between one end and the other end of each spiral coil.

In addition, in the conductive textile-based inductance-type electrode apparatus for bio-signal detection according to an embodiment of the present disclosure, a plurality of other electrode units ray be laminated in order on each electrode unit disposed at the electrode-mounted textile sheet.

In addition, in the conductive textile-based inductance-type electrode apparatus for bio-signal detection according to an embodiment of the present disclosure, an insulating member may be inserted and disposed between the electrode units adjacently laminated.

In addition, in the conductive textile-based inductance-type electrode apparatus for bio-signal detection according to an embodiment of the present disclosure, among the spiral coils adjacently laminated, one end of the spiral coil close to the skin may be connected to the other end of the spiral coil far from the skin.

In addition, in the conductive textile-based inductance-type electrode apparatus for bio-signal detection according to an embodiment of the present disclosure, among the laminated spiral coil, the oscillation signal may be input between the other end of the spiral coil closest to the skin and one end of the spiral coil farthest from the skin.

In addition, in the conductive textile-based inductance-type electrode apparatus for bio-signal detection according to an embodiment of the present disclosure, another electrode unit may laminated on each electrode unit disposed at the electrode-mounted textile sheet, the laminated spiral coils have different turning directions, the other end of any one spiral coil is connected to the other end of another spiral coil, and the oscillation signal is input between one end of any one spiral coil and one end of another spiral coil.

In addition, in the conductive textile-based inductance-type electrode apparatus for bio-signal detection according to an embodiment of the present disclosure, the textile electrode may output a signal of any one of a heartbeat, an electrocardiogram (ECG), a breath, an electromyogram, a brainwave and a body composition of a subject person.

In addition, in the conductive textile-based inductance-type electrode apparatus for bio-signal detection according to an embodiment of the present disclosure, the spiral coil may have a turn number of 8 to 12.

Other features and aspects will be apparent from the following detailed description with respect to the drawings.

Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

If the conductive textile-based inductance-type electrode apparatus for bio-signal detection according to the present disclosure is used, a coil-type magnetic field sensor is located in a planar or three-dimensional structure on a textile to form an inductance-type bio-signal textile electrode, buffering members are located between the inductance-type bio-signal textile electrode and the skin, and the buffering members are provided to form a predetermined space, thereby reducing a motion artefact during a signal detection process.

In addition, if the conductive textile-based inductance-type electrode apparatus for bio-signal detection according to the present disclosure is used, conductive thread-based or conductive textile-based coil-type magnetic field sensors for detecting a volume change of a living tissue by using an inductance variation are located in a planar or three-dimensional structure on a textile, thereby allowing a bio signal to detected more easily, more conveniently and more accurately.

Moreover, if the conductive textile-based inductance-type electrode apparatus for bio-signal detection according to the present disclosure is used, inductance-type bio-signal measurement electrodes are located in a planar or three-dimensional structure on a textile so that the apparatus may be worn by a bent portion of a body and a motion artefact may be reduced.

Further, the conductive textile-based inductance-type electrode apparatus for bio-signal detection according to the present disclosure may include an inductance-type bio-signal textile electrode and a textile-based connector for connecting a power to the inductance-type bio-signal textile electrode, and the textile-based connector includes a textile electrode coupling unit and a detector coupling unit, so that a power may be simply connected to or disconnected from the inductance-type bio-signal textile electrode by attaching or detaching the coupling unit, thereby reducing a power loss and allowing a signal to be detected at a desired time.

In addition, if the conductive textile-based inductance-type electrode apparatus for bio-signal detection according to the present disclosure is used, an interval is formed between the surface of a cloth in contact with the skin, or the surface of the conductive textile-based inductance-type electrode apparatus for bio-signal detection, and an electrode unit by means of a buffering member so as to have a three-dimensional structure in which the inductance-type bio-signal textile electrode does not easily move in spite of a movement of a subject person, thereby reducing an influence of a motion artefact.

BRIEF DESCRIPTION OF THE DRAWINGS

FIG. 3b is a diagram for explaining a role of a buffering member in the conductive textile-based inductance-type electrode apparatus for bio-signal detection of FIG. 3a.

FIG. 4a is a diagram for explaining a connector unit in the conductive textile-based inductance-type electrode apparatus for bio-signal detection of FIG. 3a.

FIG. 7a is a diagram for explaining a connection of each single textile electrode in the vertical array-type electrode unit of FIG. 6a.

DETAILED DESCRIPTION OF EMBODIMENTS

Hereinafter, a conductive textile-based inductance-type electrode apparatus for bio-signal detection according to the present disclosure will be described in detail with reference to the accompanying drawings.

Figure 1:
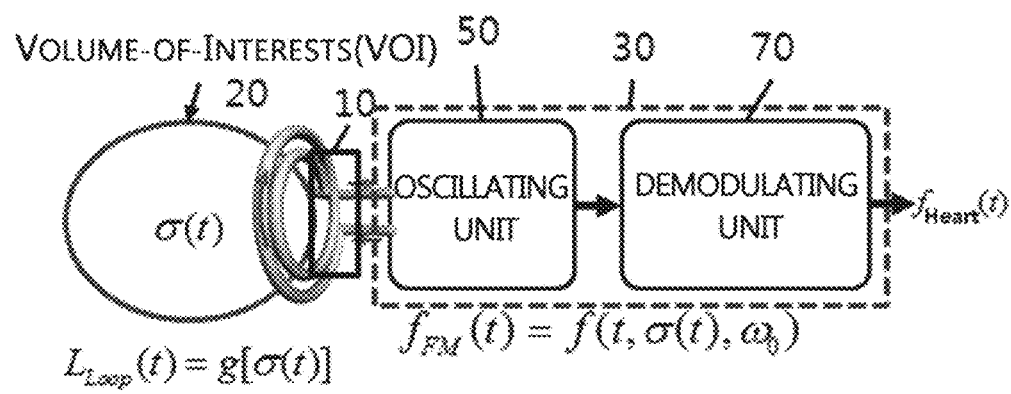
FIG. 1 is a diagram for illustrating a concept of a conductive textile-based inductance-type bio-signal measurement sensor disclosed in Korean Patent Registration No. 10-1302600.
Figure 2:
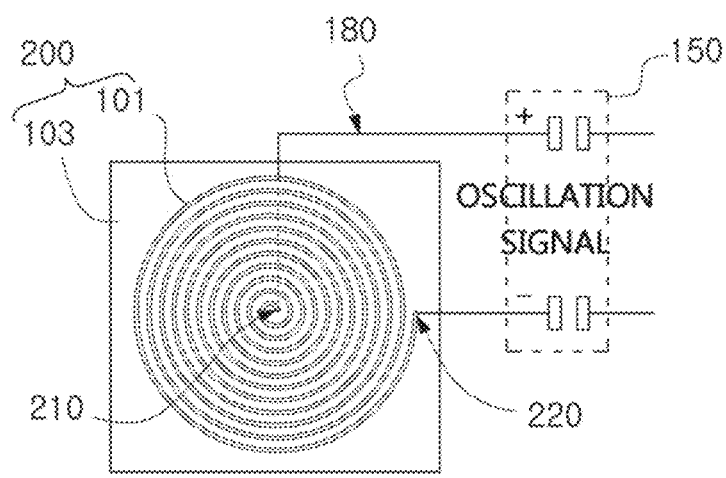
FIG. 2 is a diagram for illustrating an inductance-type bio-signal textile electrode according to an embodiment of the present disclosure.

FIG. 2 is a diagram for illustrating an inductance-type bio-signal textile electrode according to an embodiment of the present disclosure. Hereinafter, the inductance-type bio-signal textile electrode will also be called a textile electrode.

A textile electrode 200 is formed by disposing a spiral coil 101 on a textile sheet 103. Here, the spiral coil 101 is formed by spirally turning a coil thread with conductivity from one end 220 toward the other end 210. Thus, one end 220 of the spiral coil 101 is disposed at an outer portion, and the other end 210 is disposed at a center portion of the spiral coil 101.

At this time, an oscillation signal transmitted from an oscillating unit is input between the one end 220 and the other end 210 of the spiral coil 101. Therefore, a signal line 180 connected to the other end 210 of the spiral coil 101 is connected through a textile sheet 103 to a connector unit 150 in order to avoid a short of a signal.

The coil threads of the spiral coil 101 are spaced apart from each other by a predetermined distance, and on occasions, an insulating material such as cloth or silicon may fill a space between the coil threads.

The spiral coil 101 may be fabricated by embroidering, weaving or knitting a conductive yarn, fabricated by adhering a conductive material to the textile sheet 103, or fabricated by printing a conductive material to the textile sheet 103. Or else, on occasions, a conductive thread or electric wire may be located with a coil pattern on the textile sheet 103 and then adhered thereto by an adhesive or coated with an insulation material.

Figure 3A:
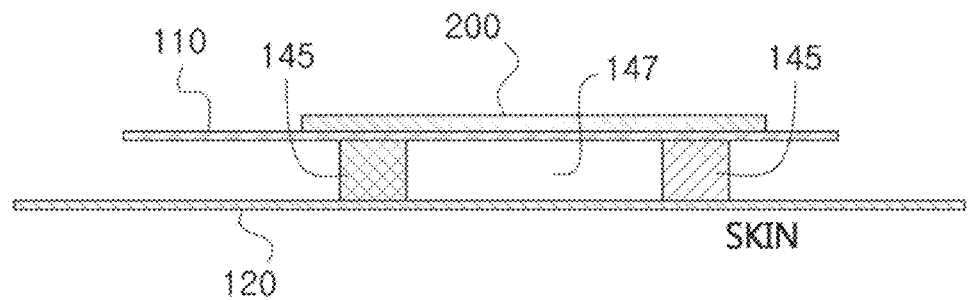
FIG. 3a is a diagram for illustrating a conductive textile-based inductance-type electrode apparatus for bio-signal detection, to which the inductance-type bio-signal textile electrode of FIG. 2 is applied.
Figure 3B:
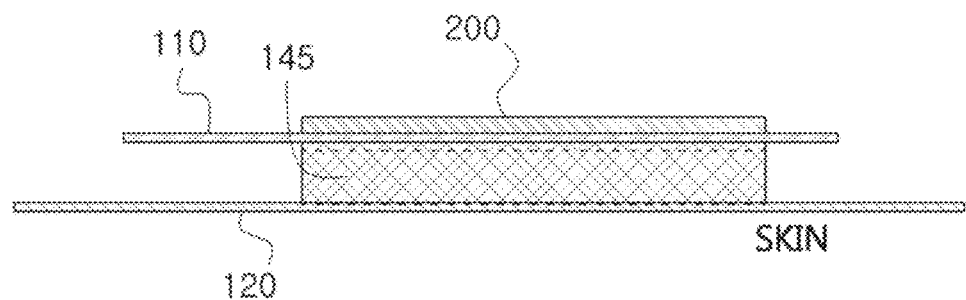
Figure 3C:
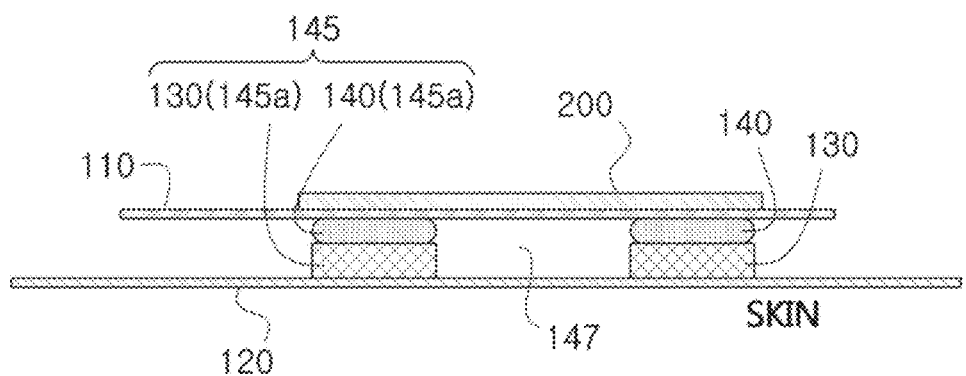
FIG. 3c is a diagram for explaining a conductive textile-based inductance-type electrode apparatus for bio-signal detection, which includes a lamination-type buffering member, as another example of the conductive textile-based inductance-type electrode apparatus for bio-signal detection of FIG. 2.

FIG. 3a is a diagram for illustrating a conductive textile-based inductance-type electrode apparatus for bio-signal detection, to which the inductance-type bio-signal textile electrode of FIG. 2 is applied, FIG. 3b is a diagram for explaining a role of a buffering member in the conductive textile-based inductance-type electrode apparatus for bio-signal detection of FIG. 3a, and FIG. 3c is a diagram for explaining a conductive textile-based inductance-type electrode apparatus for bio-signal detection, which includes a lamination-type buffering member, as another example of the conductive textile-based inductance-type electrode apparatus for bio-signal detection of FIG. 2.

As shown in FIG. 3a, the conductive textile-based inductance-type electrode apparatus for bio-signal detection of the present disclosure includes an electrode-mounted textile sheet 110, a bottom textile sheet 120, a buffering member 145 and a textile electrode 200.

The textile electrode 200 is used for detecting a bio signal and is composed of a non-contact electrode which does not come into direct contact with the skin but detects a bio signal through a coil-type magnetic field sensor.

The textile electrode 200 is disposed on the electrode-mounted textile sheet 110, buffering members 145 are located below the electrode-mounted textile sheet 110, and a bottom textile sheet 120 is located below the buffering members 145. The buffering members 145 are spaced apart from each other to form a space among the buffering members 145, and in the present disclosure, this space is called a discontinuous space 147 in which the buffering members 145 are not continuous.

The electrode-mounted textile sheet 110 may be made of a non-extendable textile. The electrode-mounted textile sheet 110 may be a textile sheet at which the spiral coil of the textile electrode 200 is formed, and, on occasions, this textile sheet may be a separate textile sheet different from the textile sheet of the textile electrode 200. On occasions, the electrode-mounted textile sheet 110 or the bottom textile sheet 120 may be a fabric mounted to cloth.

The bottom textile sheet 120 is a textile sheet which comes into contact with the skin of a human body. The skin of a human body is not flat but has bent portions, and its shape changes according to a movement of the body. Therefore, the bottom textile sheet 120 may be made of flexible material so as to bend according to a curved skin and also bent according to a movement of the body. In addition, the textile sheet of the textile electrode 200 may be made of flexible material so as to correspond to a movement of the body.

The buffering member 145 is made of electrode stabilizing foam and is mounted to lessen an influence caused by a movement of the body, namely to reduce a motion artefact, even though the textile electrode 200 is located at a bent portion of the human body.

The buffering member 145 separates the textile electrode 200 from the skin to lessen a movement of the human body, namely a movement of the skin, and may be made of any buffering material such as ethylene-vinyl acetate copolymer (EVA), Styrofoam, latex, memory foam or the like. The buffering member 145 is located between the electrode-mounted textile sheet 110 and the bottom textile sheet 120 at a position corresponding to the textile electrode 200. At least one buffering member 145 may be mounted to be spaced apart from each other in a horizontal direction, and a plurality of sub members 145a may be laminated. FIG. 3a depicts two buffering members 145, but this is just for convenience, and the present disclosure is not limited thereto.

As shown in FIG. 3b, if a single buffering member 145 is provided, the buffering member 145 serves as a single continuous material to receive a movement of a human body from the entire bottom of the buffering member 145 and a portion in contact with the skin, and this movement is transferred through the top surface of the single buffering member 145 to the textile electrode 200. In other words, a motion artefact is transferred to the textile electrode 200 through the entire area of the buffering member 145.

However, if several buffering members 145 having a small area are arranged to be spaced apart from each other as shown in FIG. 3a, a discontinuous space 147 formed by the spaced buffering members 145 is not a continuous portion of the buffering member 145 and thus the motion artefact is not transferred. As a result, a motion artefact transferred to the textile electrode 200 decreases as much as a reduced area.

In the present disclosure, the buffering members 145 having a small area may be located to be spaced apart from each other, and a plurality of sub members 145a may be laminated in a single buffering member.

In other words, as shown in FIG. 3c, the buffering member 145 may be formed by laminating a first buffering member 140 and a second buffering member 130, which serve as sub members 145a. In FIG. 3c, the first buffering member 140 is located below the electrode-mounted textile sheet 110, the second buffering member 130 is located below the first buffering member 140, and the bottom textile sheet 120 is located below the second buffering member 130. In other words, the second buffering member 130 is attached onto the bottom textile sheet 120, and the first buffering member 140 is attached below the electrode-mounted textile sheet 110.

Since the first buffering member 140 and the second buffering member 130 are separated to form a discontinuous space, a motion artefact transferred from the bottom textile sheet 120 in contact with the skin is transferred to the second buffering member 130. In addition, since a discontinuous surface exists between the first buffering member 140 and the second buffering member 130, a motion artefact reduced by the discontinuous surface is transferred from the second buffering member 130 to the first buffering member 140. In other words, if the bottom textile sheet 120 moves, the second buffering member 130 moves accordingly, but since the second buffering member 130 and the first buffering member 140 are discontinuous from each other, the first buffering member 140 is less influenced by a movement of the second buffering member 130, namely a movement of the skin.

Figure 4A:
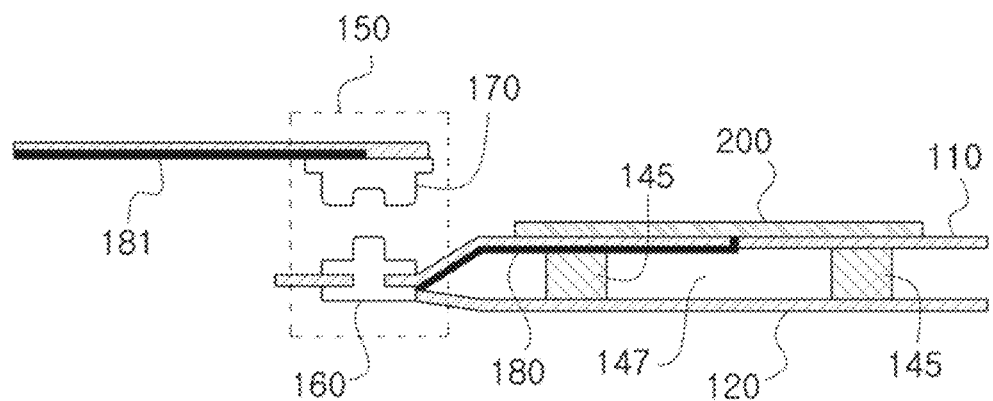
Figure 4B:
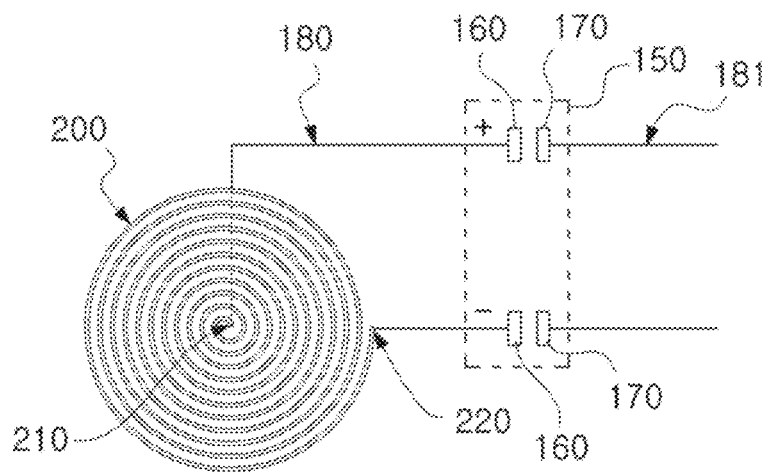
FIG. 4b is a diagram for explaining a connection state of a connector unit, in the textile electrode of FIG. 2.
Figure 5:
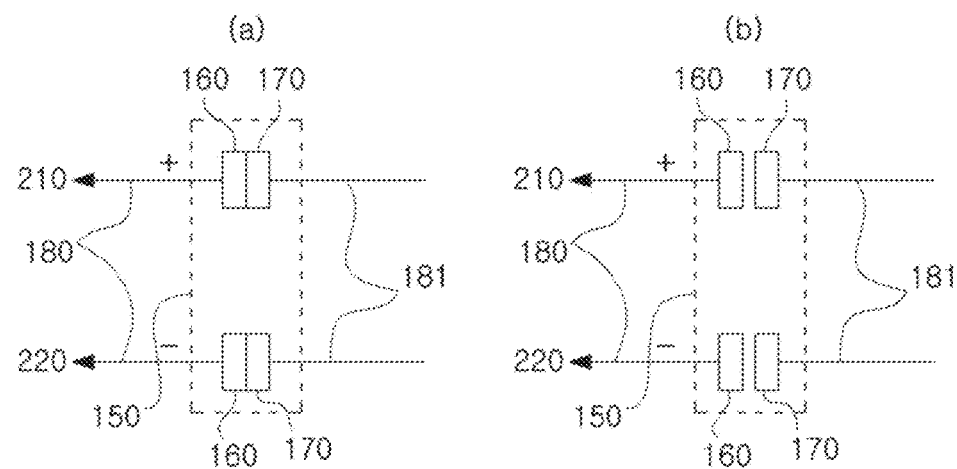
FIG. 5 is a diagram for explaining a connection or disconnection of the connector unit of FIG. 4b.

FIG. 4a is a diagram for explaining a connector unit in the conductive textile-based inductance-type electrode apparatus for bio-signal detection of FIG. 3a, FIG. 4b is a diagram for explaining a connection state of a connector unit, in the textile electrode of FIG. 2, and FIG. 5 is a diagram for explaining a connection or disconnection of the connector unit of FIG. 4b.

In the conductive textile-based inductance-type electrode apparatus for bio-signal detection, the connector unit 150 includes a textile electrode coupling unit 160 and a detector coupling unit 170.

In the spiral coil of the textile electrode 200, one end 220 of the spiral coil and the other end 210 of the spiral coil are respectively connected to a signal line 180, and each signal line connected to one end 220 of the spiral coil and the other end 210 of the spiral coil is connected to each textile electrode coupling unit 160. The detector coupling unit 170 is connected to an oscillating unit or a signal pre-processing unit by means of a connection line 181. Each textile electrode coupling unit 160 is coupled to a corresponding detector coupling unit 170, thereby connecting the textile electrode 200 to the oscillating unit or the signal pre-processing unit. In addition, due to attachment or detachment of the connector unit 150, the textile electrode coupling unit 160 serves as a switch for connecting (electric connection) or disconnecting (electric disconnection) the textile electrode 200 to/from the oscillating unit or the signal pre-processing unit.

In FIG. 4a, the textile electrode coupling unit 160 is depicted as a male coupling unit, and the detector coupling unit 170 is depicted as a connector unit 150 of a snap button type which is a female coupling unit. However, this is just for convenient explanation of the present disclosure, and the present disclosure is not limited thereto. In the present disclosure, the textile electrode coupling unit 160 may be a female coupling unit, the detector coupling unit 170 may be a male coupling unit, and the connector unit 150 may be various kinds of connectors. Therefore, the connector unit 150 may be any one of a button, a buckle, a clip, a hook, a conductive Velcro, a conductive zipper, a conductive cord, a conductive thread, a conductive textile, or other subsidiary members.

As shown in (a) of FIG. 5, the connector unit 150 is electrically connected by uniting the textile electrode coupling unit 160 and the detector coupling unit 170. In other words, the connector unit 150 is electrically connected when the textile electrode coupling unit 160 mounted to an end of the signal line 180 connected to the other end 210 of the spiral coil is coupled to the detector coupling unit 170 connected to the oscillating unit or the signal pre-processing unit. In this case, the oscillation signal from the oscillating unit is transferred to the spiral coil of the textile electrode 200, and the output signal of the textile electrode 200 is transferred to the signal pre-processing unit.

As shown in (b) of FIG. 5, if the textile electrode coupling unit 160 and the detector coupling unit 170 are separated from each other, an electric disconnection is established. In other words, if the textile electrode coupling unit 160 mounted to an end of the signal line 180 connected to the other end 210 of the spiral coil is separated from the detector coupling unit 170 connected to the oscillating unit or the signal pre-processing unit, the oscillation signal from the oscillating unit is not transferred to the spiral coil of the textile electrode 200 any more, and the output signal of the textile electrode 200 is not transferred to the signal pre-processing unit any more.

In the present disclosure, an array-type inductance-type bio-signal textile electrode (hereinafter, also referred to as an array-type textile electrode) may configure a vertical array-type electrode unit by laminating a plurality of single textile electrodes. In other case, a plurality of single textile electrodes may be horizontally arranged to configure a horizontal array-type electrode unit. In other case, a plurality of vertical array-type electrode units may be horizontally arranged to configure a vertical and horizontal array-type electrode unit.

Figure 6A:
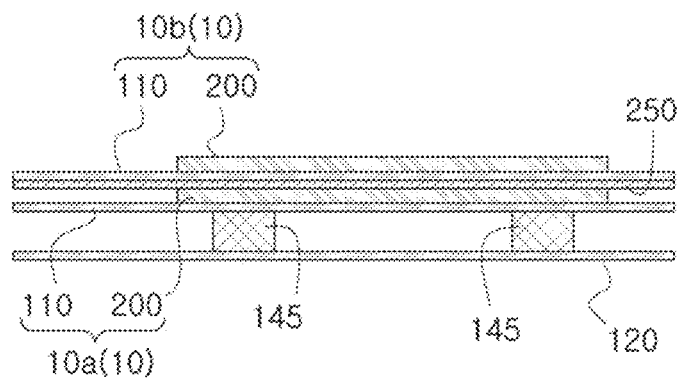
FIG. 6a is a diagram for explaining a vertical array-type electrode unit according to an embodiment of the present disclosure.
Figure 6B:
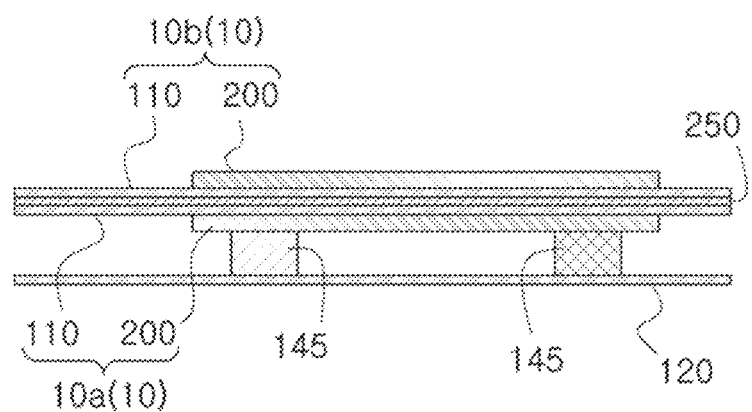
FIG. 6b is a diagram for explaining a vertical array-type electrode unit according to another embodiment of the present disclosure.

FIG. 6a is a diagram for explaining a vertical array-type electrode unit according to an embodiment of the present disclosure, and FIG. 6b is a diagram for explaining a vertical array-type electrode unit according to another embodiment of the present disclosure.

In FIGS. 6a and 6b, a buffering member 145 is located on the bottom textile sheet 120, a plurality of electrode units 10 such as a first electrode unit 10a and a second electrode unit 10b is laminated thereon, and an insulating member 250 is interposed between the electrode units 10. The insulating member 250 may be an insulating textile or other materials such as silicon, sponge, memory foam or the like. The electrode unit 10 (the first electrode unit 10a and the second electrode unit 10b in FIG. 6) formed by laminating a plurality of electrode units 10 may be called an array-type electrode unit. On occasions, the insulating member 250 may be formed by pouring molten silicon on a rear side of the electrode-mounted textile sheet 110 and coating thereto.

In FIG. 6a, the buffering member 145 is located on the bottom textile sheet 120, the electrode-mounted textile sheet 110 of the first electrode unit 10a is located thereon, the textile electrode 200 of the first electrode unit 10a is located on the electrode-mounted textile sheet 110 of the first electrode unit 10a, the insulating member 250 is located thereon, the electrode-mounted textile sheet 110 of the second electrode unit 10b is located thereon, and the textile electrode 200 of the second electrode unit 10b is located on the electrode-mounted textile sheet 110 of the second electrode unit 10b.

In FIG. 6b, the buffering member 145 is located on the bottom textile sheet 120, the textile electrode 200 of the first electrode unit 10a is located thereon, the electrode-mounted textile sheet 110 of the first electrode unit 10a is located on the textile electrode 200 of the first electrode unit 10*a*, the insulating member 250 is located thereon, the electrode-mounted textile sheet 110 of the second electrode unit 10*b* is located thereon, and the textile electrode 200 of the second electrode unit 10*b* is located on the electrode-mounted textile sheet 110 of the second electrode unit 10*b*. On occasions, in FIG. 6*b*, the electrode-mounted textile sheet 110 and the insulating member 250 of the first electrode unit 10*a* and the electrode-mounted textile sheet 110 of the second electrode unit 10*b* may be configured using a single textile sheet, and the coil of the textile electrode 200 of the first electrode unit 10*a* and the coil of the textile electrode 200 of the second electrode unit 10*b* may be located at both sides of a single textile sheet and formed by adhesion using silicon or the like.

As shown in FIGS. 6*a* and 6*b*, due to the coil of the laminated textile electrode 200, a generated magnetic field will increase further, and resultantly a bio signal obtained from the textile electrode 200 will have a higher S/N ratio.

The vertical array-type electrode unit of FIGS. 6*a* and 6*b* may transmit an oscillation signal to each single textile electrode separately or may connect single textile electrodes to each other and transmit an oscillation signal to both ends thereof, namely a start point and an end point.

Figure 7A:
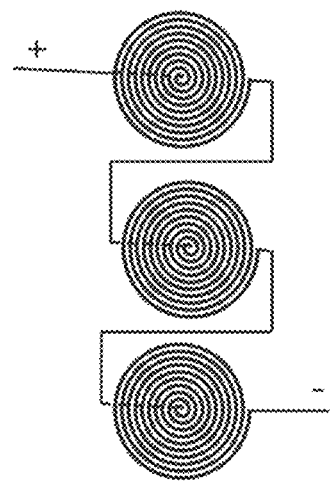
Figure 7B:
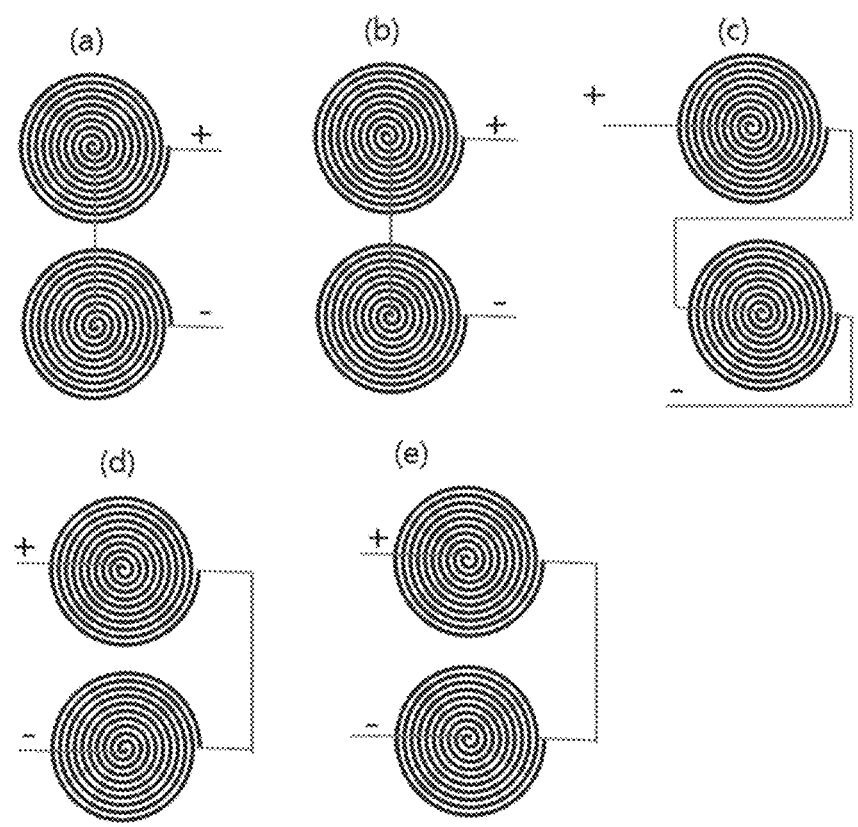
FIG. 7b is a diagram for explaining a connection of each single textile electrode in the vertical array-type electrode unit of FIG. 6b.

FIG. 7*a* is a diagram for explaining a connection of each single textile electrode in the vertical array-type electrode unit of FIG. 6*a*, and FIG. 7*b* is a diagram for explaining a connection of each single textile electrode in the vertical array-type electrode unit of FIG. 6*b*.

FIG. 7*a* shows that, in a state of FIG. 6*a*, one end of the spiral coil of a single electrode is connected to the other end of a spiral coil of a next electrode so that an oscillation signal may be transmitted to both ends thereof, namely the other end of the first spiral coil and one end of the final spiral coil.

Portion (a) of FIG. 7*b* depicts that, in a state of FIG. 6*b*, the spiral coil of the second electrode unit 10*b* and the spiral coil of the first electrode unit 10*a* have opposite turning directions, the other end of the spiral coil of the second electrode unit 10*b* is connected to the other end of the spiral coil of the first electrode unit 10*a*, and an oscillation signal is transmitted to both ends, namely one end of the spiral coil of the second electrode unit 10*b* and one end of the spiral coil of the first electrode unit 10*a*.

Portion (b) of FIG. 7*b* depicts that, in a state of FIG. 6*b*, the spiral coil of the second electrode unit 10*b* and the spiral coil of the first electrode unit 10*a* have the same turning direction, the other end of the spiral coil of the second electrode unit 10*b* is connected to the other end of the spiral coil of the first electrode unit 10*a*, and an oscillation signal is transmitted to both ends, namely one end of the spiral coil of the second electrode unit 10*b* and one end of the spiral coil of the first electrode unit 10*a*.

Portion (c) of FIG. 7*b* depicts that, in a state of FIG. 6*b*, the spiral coil of the second electrode unit 10*b* and the spiral coil of the first electrode unit 10*a* have the same turning direction, one end of the spiral coil of the second electrode unit 10*b* is connected to the other end of the spiral coil of the first electrode unit 10*a*, and an oscillation signal is transmitted to both ends, namely the other end of the spiral coil of the second electrode unit 10*b* and one end of the spiral coil of the first electrode unit 10*a*.

Portion (d) of FIG. 7*b* depicts that, in a state of FIG. 6*b*, the spiral coil of the second electrode unit 10*b* and the spiral coil of the first electrode unit 10*a* have opposite turning directions, one end of the spiral coil of the second electrode unit 10*b* is connected to one end of the spiral coil of the first electrode unit 10*a*, and an oscillation signal is transmitted to both ends, namely the other end of the spiral coil of the second electrode unit 10*b* and the other end of the spiral coil of the first electrode unit 10*a*.

Portion (e) of FIG. 7*b* depicts that, in a state of FIG. 6*b*, the spiral coil of the second electrode unit 10*b* and the spiral coil of the first electrode unit 10*a* have the same turning direction, one end of the spiral coil of the second electrode unit 10*b* is connected to one end of the spiral coil of the first electrode unit 10*a*, and an oscillation signal is transmitted to both ends, namely the other end of the spiral coil of the second electrode unit 10*b* and the other end of the spiral coil of the first electrode unit 10*a*.

Figure 8:
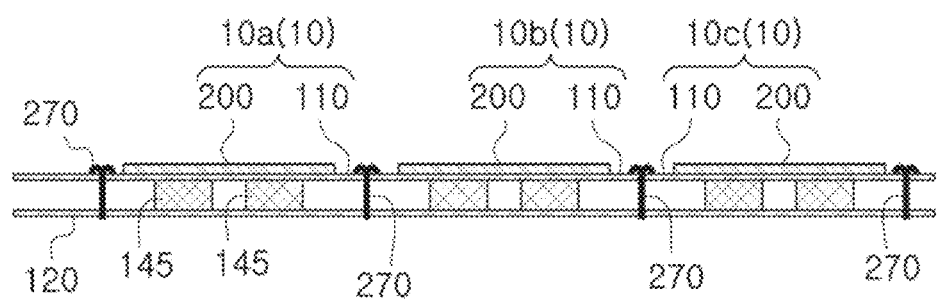
FIG. 8 is a diagram for explaining a horizontal array-type electrode unit according to an embodiment of the present disclosure.
Figure 9:
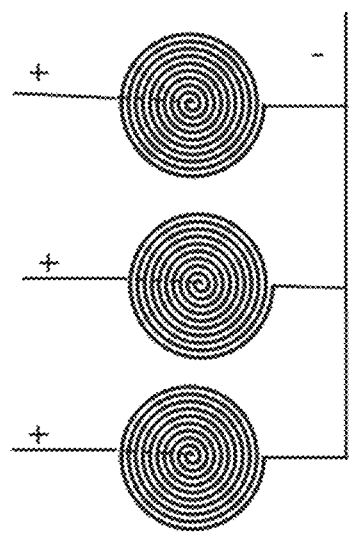
FIG. 9 is a diagram for explaining a connection of each single textile electrode in the horizontal array-type electrode unit according to an embodiment of the present disclosure.

FIG. 8 is a diagram for explaining a horizontal array-type electrode unit according to an embodiment of the present disclosure, and FIG. 9 is a diagram for explaining a connection of each single textile electrode in the horizontal array-type electrode unit according to an embodiment of the present disclosure.

A horizontal array-type electrode unit includes a plurality of horizontal electrode units 10, and the plurality of electrode units 10 may be configured to share the electrode-mounted textile sheet 110 and the bottom textile sheet 120. In other words, the electrode units 10, for example first to third electrode units 10*a* to 10*c*, respectively have a buffering member 145 located on the bottom textile sheet 120, a shared electrode-mounted textile sheet 110 is located thereon, and each textile electrode 200 is located thereon. In this case, the horizontal array-type electrode unit may connect the plurality of electrode units 10 to each other by means of sewing 270 or adhesion, and the electrode-mounted textile sheet 110 of the electrode units 10 may be separated from each other.

By using the textile electrode 200 horizontally located as described above, a bio signal input as a differential signal at an input terminal, a bio signal demanding a plurality of signal electrodes or the like may be detected.

In case of the horizontal array-type electrode unit of FIG. 8, similar to FIG. 7*a*, the spiral coils of the textile electrodes 200 are connected so that an oscillation signal may be transmitted to the other end of the first spiral coil and one end of the final spiral coil. However, as shown in FIG. 9, it is also possible that an oscillation signal is transmitted to each textile electrode, namely each spiral coil. In FIG. 9, an oscillation signal is transmitted to both ends, namely one end and the other end, of the spiral coil of each textile electrode.

The electrode unit (the first to third electrode units 10*a* to 10*c* in FIG. 8) configured by horizontally installing a plurality of electrode units 10 may be called an array electrode unit.

Figure 10:
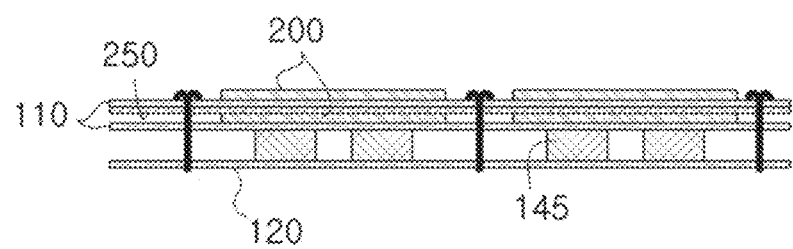
FIG. 10 is a diagram for explaining a vertical and horizontal array-type electrode unit according to an embodiment of the present disclosure.
Figure 10:
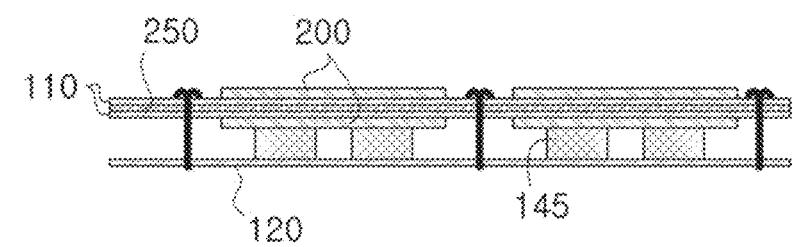
Figure 11:
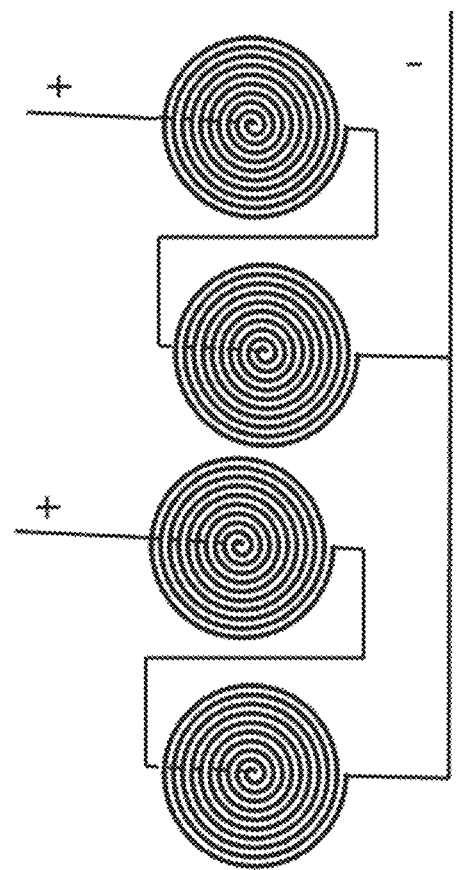
FIG. 11 is a diagram for explaining a connection of each single textile electrode in the vertical and horizontal array-type electrode unit according to an embodiment of the present disclosure.

FIG. 10 is a diagram for explaining a vertical and horizontal array-type electrode unit according to an embodiment of the present disclosure, and FIG. 11 is a diagram for explaining a connection of each single textile electrode in the vertical and horizontal array-type electrode unit according to an embodiment of the present disclosure.

As shown in Portions (a) and (b) of FIG. 10, a plurality of vertical array-type electrode units may be horizontally located to configure a vertical and horizontal array-type electrode unit. In this case, as shown in FIG. 11, a coil of each textile electrode 200 may be connected to each vertical array-type electrode unit so that an oscillation signal may be transmitted to both ends, namely the other end of the first spiral coil and one end of the final spiral coil. Though not shown in the figure, upper and lower coils may have opposite polarities based on the insulating member, the other ends thereof may be connected, and an oscillation signal may be transmitted to both one ends.

Figure 12:
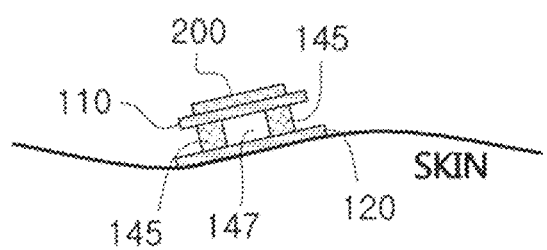
FIG. 12 is a diagram for explaining a role of a buffering member in the conductive textile-based inductance-type electrode apparatus for bio-signal detection to which the textile electrode of the present disclosure is applied.

FIG. 12 is a diagram for explaining a role of a buffering member in the conductive textile-based inductance-type electrode apparatus for bio-signal detection to which the textile electrode of the present disclosure is applied.

If the textile electrode 200 is located on a bent skin of the human body, artefact such as an artifact (motion artefact) caused by a behavior of a subject person is greater than a case where the textile electrode 200 is located on a flat portion of the human body, and thus a signal may not be normally detected. To supplement this, in the present disclosure, the buffering member 145 is interposed between the textile electrode 200 and the skin of the human body so that the textile electrode 200 is stabilized without moving, thereby primarily reducing a motion artefact detected by the textile electrode 200. In addition, in the present disclosure, by decreasing a width of the buffering member 145 and placing a space, namely a discontinuous space 147, between the buffering member 145 and the buffering member 145, a motion artefact transferred through the buffering member 145 to the textile electrode 200 is minimized.

Figure 13:
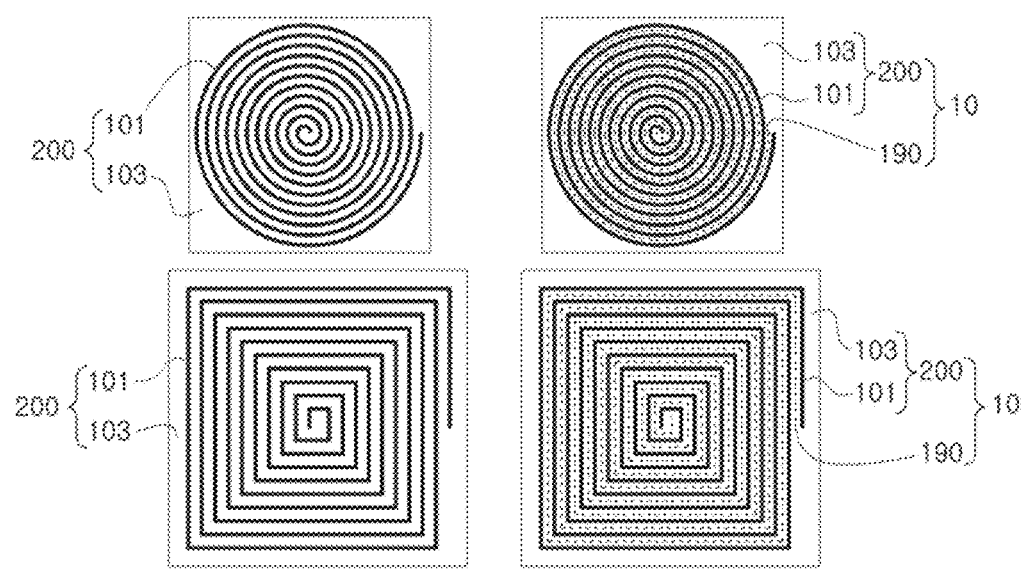
FIG. 13 shows examples of the textile electrode of the present disclosure.

FIG. 13 shows examples of the textile electrode of the present disclosure.

The textile electrode 200 of the present disclosure is a non-contact electrode, and a spiral coil 101 of various shapes such as circular and rectangular shapes may be formed on the textile sheet 103. Portions (a) and (b) of FIG. 13 show that the spiral coil 101 is formed by spirally turning a coil thread into a circular shape on the textile sheet 103, and Portions (c) and (d) of FIG. 13 depicts that the spiral coil 101 is formed by spirally turning a coil thread into a rectangular shape on the textile sheet 103. Here, even though just circular and rectangular shapes are depicted, the present disclosure is not limited thereto, but the spiral coil 101 of the present disclosure may have various shapes such as rectangular and diamond shapes.

As shown in Portions (b) and (d) of FIG. 13, the electrode unit 10 may further include an anti-contact unit 190. The anti-contact unit 190 prevents adjacent coil threads from coming into contact with each other and is disposed between adjacent coil threads while turning together with the coil thread. The anti-contact unit 190 is stitched using an insulating thread between the coil threads, but the present disclosure is not limited thereto, and an insulating material may be inserted between the coil threads by printing or adhesion. In other case, the textile sheet 103 of the textile electrode 200 may also be embossed by means of thermal or chemical treatment, and the coil thread may also be coated with an insulation material.

Figure 14:
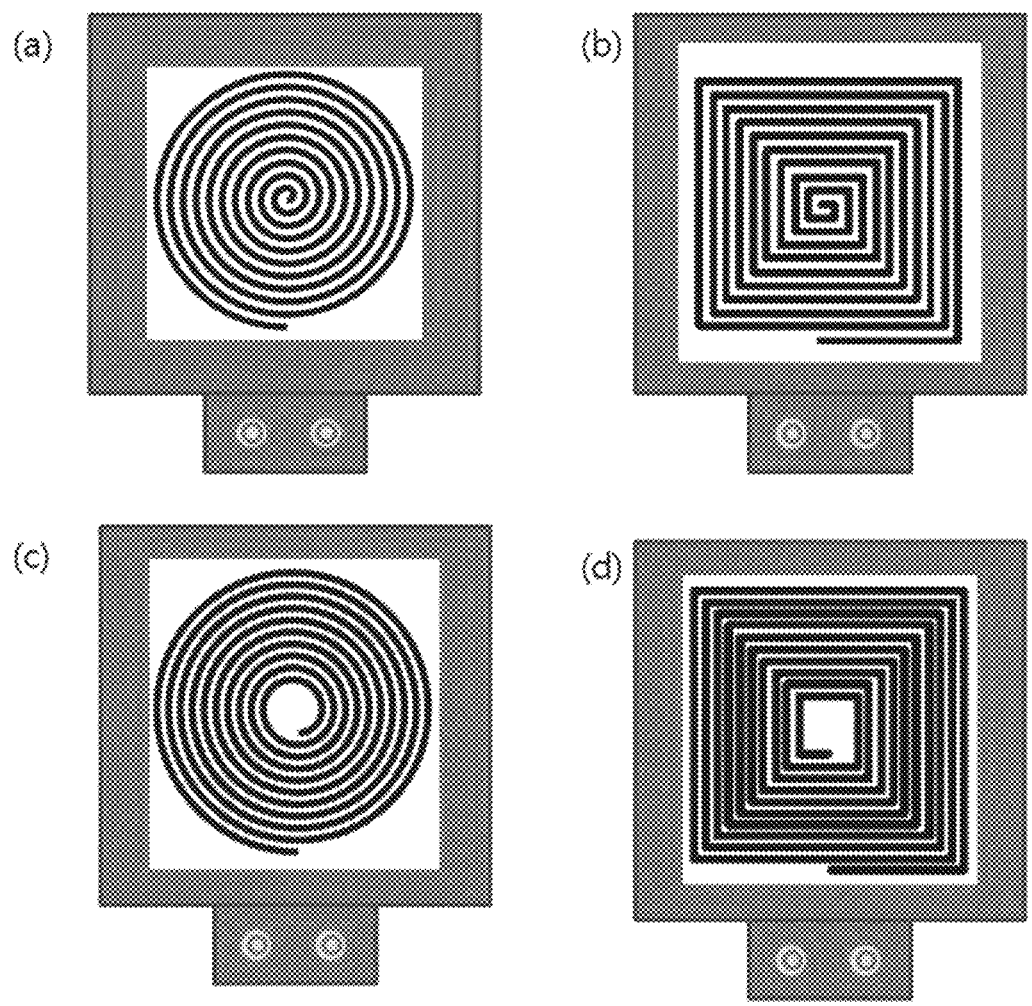
FIG. 14 shows an example of the conductive textile-based inductance-type electrode apparatus for bio-signal detection including the single textile electrode of the present disclosure.

FIG. 14 shows an example of the conductive textile-based inductance-type electrode apparatus for bio-signal detection including the single textile electrode of the present disclosure.

In Portion (a) of FIG. 14, a circular spiral coil is provided, so that the other end thereof is disposed at a center portion and one end is disposed at an outer portion.

In Portion (b) of FIG. 14, a rectangular spiral coil is provided, so that the other end thereof is disposed at a center portion and one end is disposed at an outer portion.

In Portion (c) of FIG. 14, a circular doughnut-type spiral coil is provided, so that a hole is formed at, and the other end thereof is disposed at a center portion (in more detail, an outer region of the central hole) and one end is disposed at an outer portion.

In Portion (d) of FIG. 14, a rectangular doughnut-type spiral coil is provided, so that a hole is formed at, and the other end thereof is disposed at a center portion (in more detail, an outer region of the central hole) and one end is disposed at an outer portion.

Figure 15:
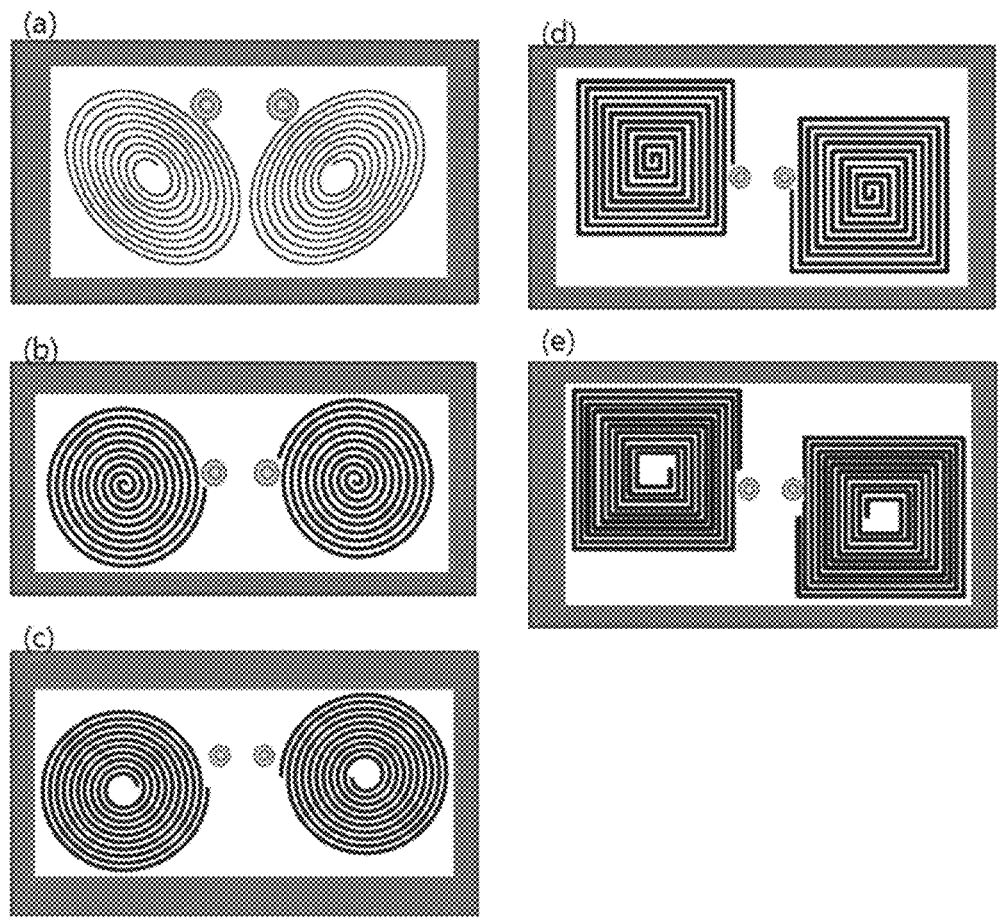
FIG. 15 shows an example of the conductive textile-based inductance-type electrode apparatus for bio-signal detection which includes the horizontal array-type electrode unit of the present disclosure.

FIG. 15 shows an example of the conductive textile-based inductance-type electrode apparatus for bio-signal detection which includes the horizontal array-type electrode unit of the present disclosure.

Portion (a) of FIG. 15 shows two oval doughnut-type textile electrodes, in which spiral coils of two textile electrodes have opposite turning directions, the other ends of the spiral coils located at the center portions of two textile electrodes are connected to each other, and an oscillation signal is input to both ends, namely one ends of the spiral coils located at outer portions of two textile electrodes. In other words, in Portion (a) of FIG. 15, one ends of the spiral coils located at outer portions of two textile electrodes are connected to the detector coupling unit to apply an oscillation signal.

Portion (b) of FIG. 15 shows two circular textile electrodes, and Portion (d) of FIG. 15 shows two rectangular textile electrodes, in which coils of two textile electrodes have opposite turning directions, the other ends of the coils at the center portions of two textile electrodes are connected to each other, and an oscillation signal is input to both ends, namely one ends of the spiral coils located at outer portions of two textile electrodes.

Portion (c) of FIG. 15 shows two circular doughnut-type textile electrodes, and Portion (e) of FIG. 15 shows two doughnut-type rectangular textile electrodes, in which coils of two textile electrodes have opposite turning directions, the other ends of the coils at the center portions of two textile electrodes are connected to each other, and an oscillation signal is input to both ends, namely one ends of the coils located at outer portions of two textile electrodes.

Figure 16:
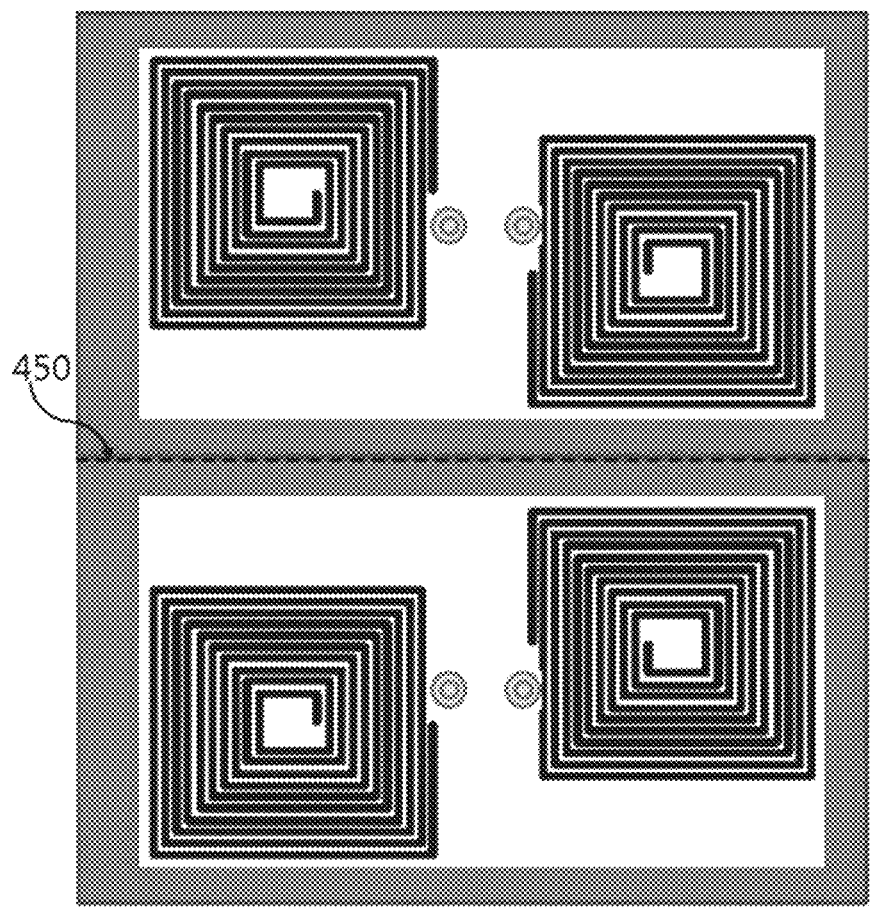
FIG. 16 shows an example of the conductive textile-based inductance-type electrode apparatus for bio-signal detection which includes the vertical and horizontal array-type electrode unit of the present disclosure.

FIG. 16 shows an example of the conductive textile-based inductance-type electrode apparatus for bio-signal detection which includes the vertical and horizontal array-type electrode unit of the present disclosure.

FIG. 16 shows an example in which two vertical array-type electrode units having two textile electrodes are provided horizontally to form a vertical and horizontal array-type electrode unit. In FIG. 16, four rectangular doughnut-type textile electrodes are provided, so that two spiral coils are provided at an upper portion and two spiral coils are provided at a lower portion, and two spiral coils at the upper portion and two spiral coils at the lower portion are folded based on a folding line 450. Regarding two spiral coils at the upper portion and two spiral coils at the lower portion, spiral coils of two textile electrodes located at the right and the left have opposite turning directions, and the other ends of a spiral coil at the upper portion and a spiral coil at the lower portion, adjacent to each other, are connected to each other.

Figure 17:
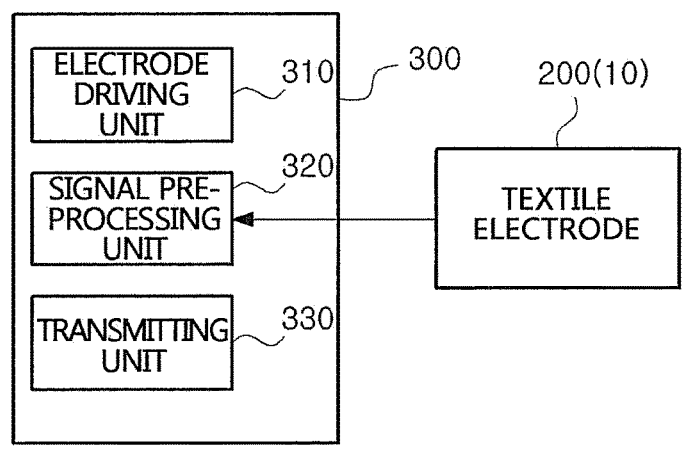
FIG. 17 is a block diagram for illustrating a signal detection module according to an embodiment of the present disclosure.

FIG. 17 is a block diagram for illustrating a signal detection module according to an embodiment of the present disclosure.

In the present disclosure, the signal detection module 300 may be located at one side of the electrode unit 10.

The signal detection module 300 includes an electrode driving unit 310, a signal pre-processing unit 320 and a transmitting unit 330.

The electrode driving unit 310 includes an osculation circuit having L and C and transmits a vibration signal to the spiral coil of the textile electrode 200. If so, a minute current flowing to the spiral coil of the textile electrode 200 forms a magnetic field. The magnetic field varying according to time induces an eddy current at a detection target (or, in a human body), and the formed induced current generates a minute magnetic field in a direction opposite to the magnetic field formed at the spiral coil of the textile electrode 200.

The signal pre-processing unit 320 includes a demodulating unit (not shown), an amplifier (not shown) and a filter (not shown), demodulates the vibration signal received from the electrode unit 10 to detect a bio signal, and amplifies the bio signal to reduce artefact. Meanwhile, the transmitting unit 330 transmits the bio signal detected by the signal pre-processing unit 320. The transmitting unit 330 may be a wireless transmitting unit or a wired transmission port for transmitting a signal in a wired manner.

Figure 18:
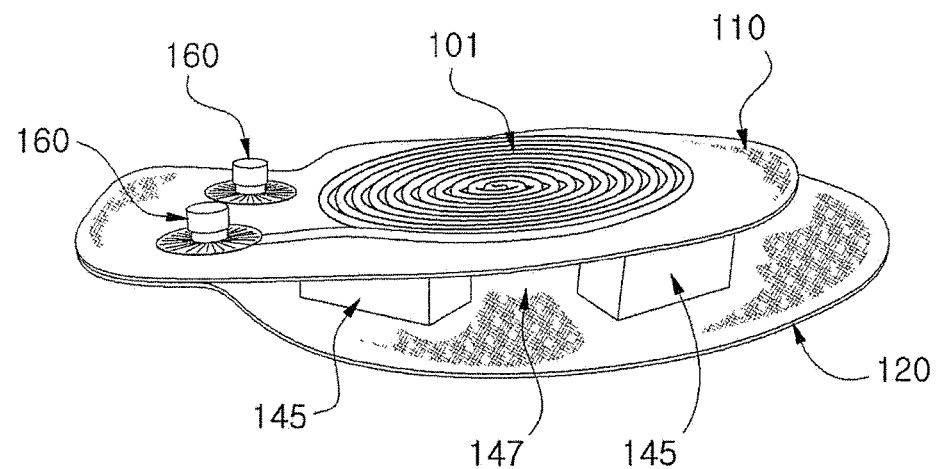
FIG. 18 shows an example of the conductive textile-based inductance-type electrode apparatus for bio-signal detection which includes the single textile electrode of the present disclosure.

FIG. 18 shows an example of the conductive textile-based inductance-type electrode apparatus for bio-signal detection which includes the single textile electrode of the present disclosure.

In FIG. 18, the spiral coil 101 is mounted on the electrode-mounted textile sheet 110, the buffering members 145 are located below the electrode-mounted textile sheet 110 to be spaced apart from each other, and the bottom textile sheet 120 is located below the buffering member 145. The discontinuous space 147 is provided between the buffering member 145 and the buffering member 145. If the center portion of the spiral coil 101 is set as the other end of the spiral coil 101 and the terminal of the spiral coil 101 located at an outer portion of the spiral coil 101 is set as one end of the spiral coil 101, the other end of the spiral coil 101 and one end of the spiral coil 101 are respectively connected to the textile electrode coupling unit 160. In order to input an oscillation signal from the oscillating unit between the other end of the spiral coil 101 and one end of the spiral coil 101, the textile electrode coupling unit 160 is connected to the detector coupling unit 170 (FIGS. 4a and 4b). Therefore, the signal line 180 (FIGS. 4a and 4b) connected to the other end of the spiral coil 101 is connected through the electrode-mounted textile sheet 110 to the textile electrode coupling unit 160.

Figure 19:
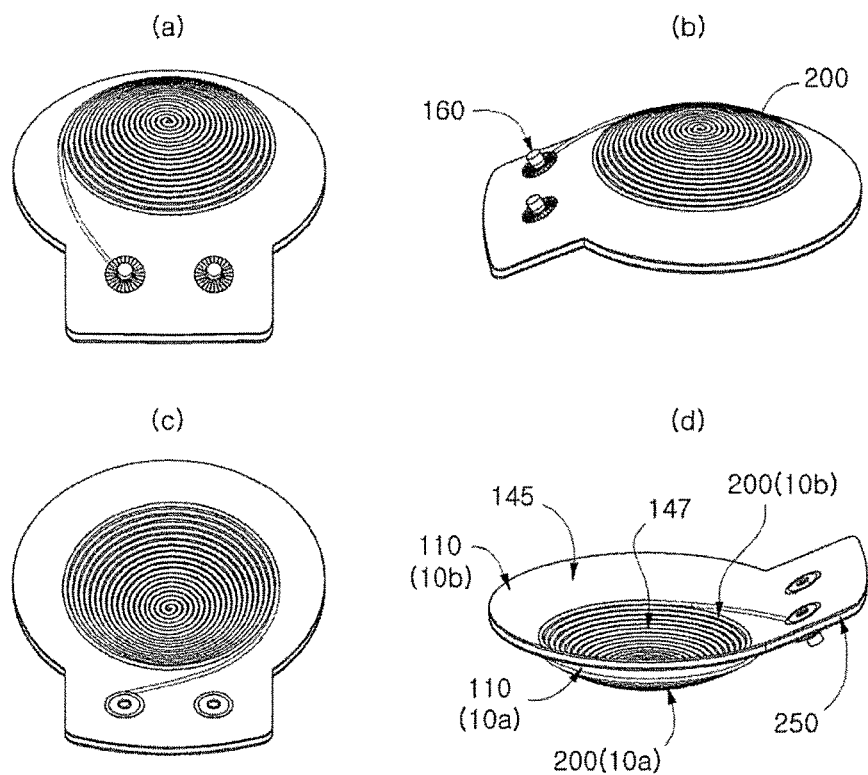
FIG. 19 shows an example of the conductive textile-based inductance-type electrode apparatus for bio-signal detection which includes the vertical array-type electrode of the present disclosure.

FIG. 19 shows an example of the conductive textile-based inductance-type electrode apparatus for bio-signal detection which includes the vertical array-type electrode of the present disclosure.

Portion (a) of FIG. 19 shows a top surface of the conductive textile-based inductance-type electrode apparatus for bio-signal detection, which includes a vertical array-type electrode unit, and Portion (b) of FIG. 19 is a side view showing the top surface of the conductive textile-based inductance-type electrode apparatus for bio-signal detection of Portion (a) of FIG. 19. Referring to Portion (b) of FIG. 19, the conductive textile-based inductance-type electrode apparatus for bio-signal detection according to the present disclosure includes the electrode-mounted textile sheet 110 on the insulating member 250, and the second electrode unit 10b having the textile electrode 200 with a spiral coil is provided thereon.

Portion (c) of FIG. 19 shows a bottom surface of the conductive textile-based inductance-type electrode apparatus for bio-signal detection, which includes a vertical array-type electrode, and Portion (d) of FIG. 19 is a side view showing the bottom surface of the conductive textile-based inductance-type electrode apparatus for bio-signal detection. Referring to Portion (d) of FIG. 19, the conductive textile-based inductance-type electrode apparatus for bio-signal detection according to the present disclosure includes the electrode-mounted textile sheet 110 below the insulating member 250, and the first electrode unit 10a having the textile electrode 200 with a spiral coil is provided below it.

In the conductive textile-based inductance-type electrode apparatus for bio-signal detection having a vertical array-type electrode unit as shown in FIG. 19, a bottom surface may be concavely depressed into a dome shape. Here, the buffering member 145 may be separately disposed along a rim of the electrode-mounted textile sheet 110 or may integrally extend from the rim of the electrode-mounted textile sheet 110. At this time, the depressed portion of the electrode-mounted textile sheet 110 forms the discontinuous space 147. Meanwhile, the conductive textile-based inductance-type electrode apparatus for bio-signal detection, which is formed in a dome shape, may be applied not only in a case where a vertical array-type electrode unit is provided but also in a case where an electrode unit having a single textile electrode, a horizontal array-type electrode unit or a vertical and horizontal array-type electrode unit is provided.

Figure 20:
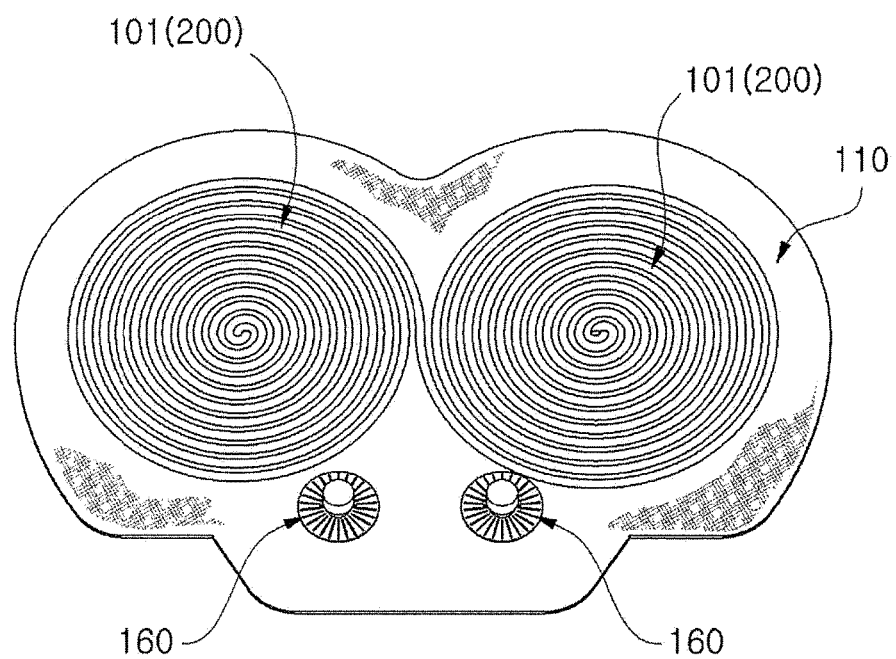
FIG. 20 shows an example of the conductive textile-based inductance-type electrode apparatus for bio-signal detection which includes the horizontal array-type electrode of the present disclosure.

FIG. 20 shows an example of the conductive textile-based inductance-type electrode apparatus for bio-signal detection which includes the horizontal array-type electrode of the present disclosure.

As shown in FIG. 20, the conductive textile-based inductance-type electrode apparatus for bio-signal detection according to the present disclosure includes two textile electrodes 200 located in parallel on a horizontal surface by mounting two spiral coils 101 to a single electrode-mounted textile sheet 110. A buffering member may be mounted below the horizontal array-type electrode unit of FIG. 20, and a bottom textile sheet may be mounted below it. FIG. 20 may have a configuration as shown in Portion (d) or (e) of FIG. 7b.

Figure 21:
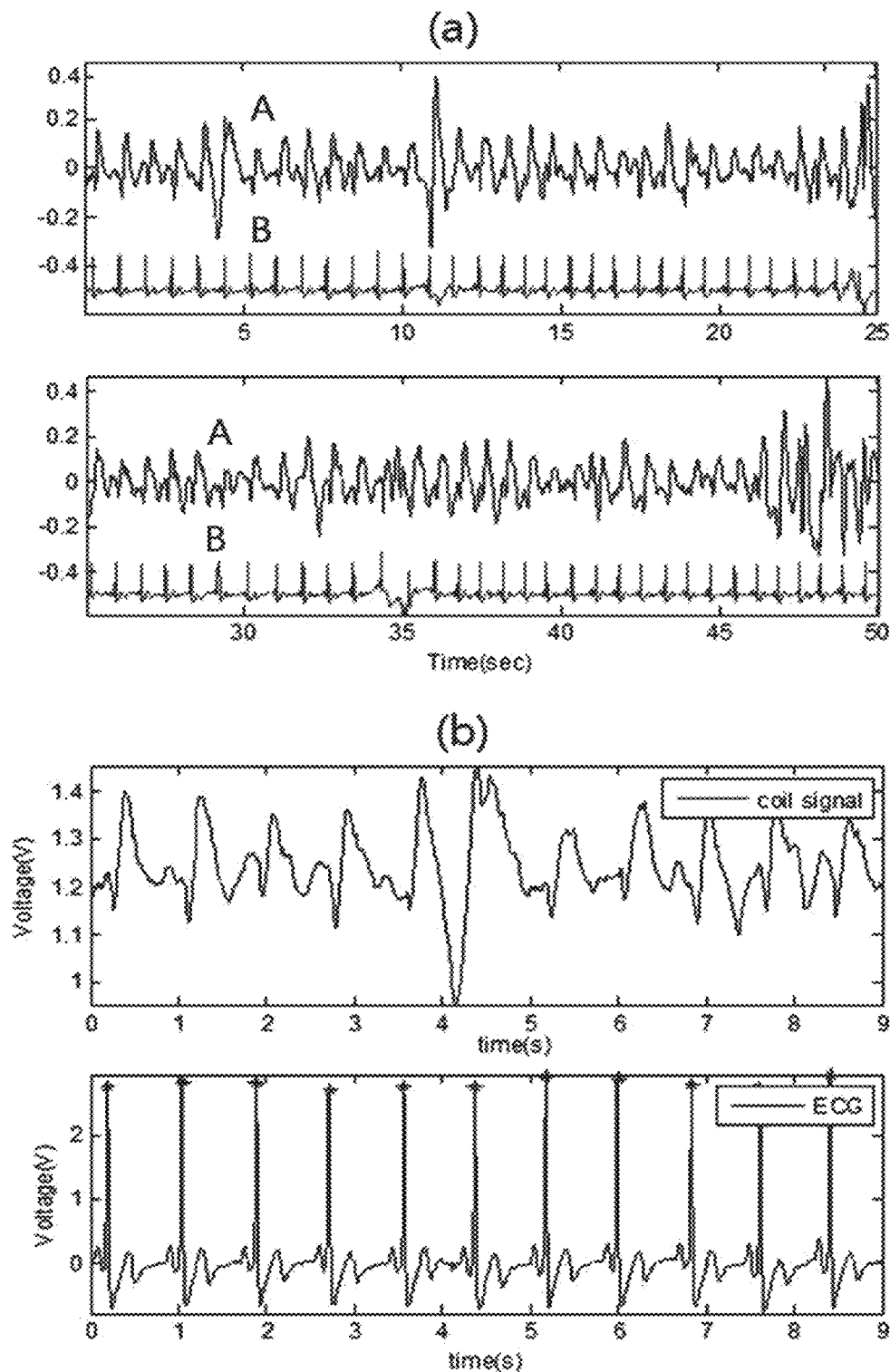
FIG. 21 shows an example of a heartbeat signal detected by the conductive textile-based inductance-type electrode apparatus for bio-signal detection which includes the single textile electrode of the present disclosure.

FIG. 21 shows an example of a heartbeat signal detected by the conductive textile-based inductance-type electrode apparatus for bio-signal detection which includes the single textile electrode of the present disclosure.

In Portion (a) of FIG. 21, a heartbeat signal (A) is detected by the single textile electrode (see FIG. 18) having a circular spiral coil, and an electrocardiogram (ECG) signal (B) is detected as a reference signal by means of an existing electrocardiogram (ECG) detection method in order to check whether the heartbeat signal is normally detected.

Portion (b) of FIG. 21 shows the heartbeat signal and the electrocardiogram (ECG) corresponding thereto, depicted in Portion (a) of FIG. 21, in a partially amplified and enlarged state. An upper graph of Portion (b) of FIG. 21 represents a heartbeat signal, and a lower graph represents an electrocardiogram (ECG) signal. From this, it can be found that a peak of the heartbeat signal is detected by synchronization with an R point (marked by '*') of the electrocardiogram (ECG) signal.

Figure 22:
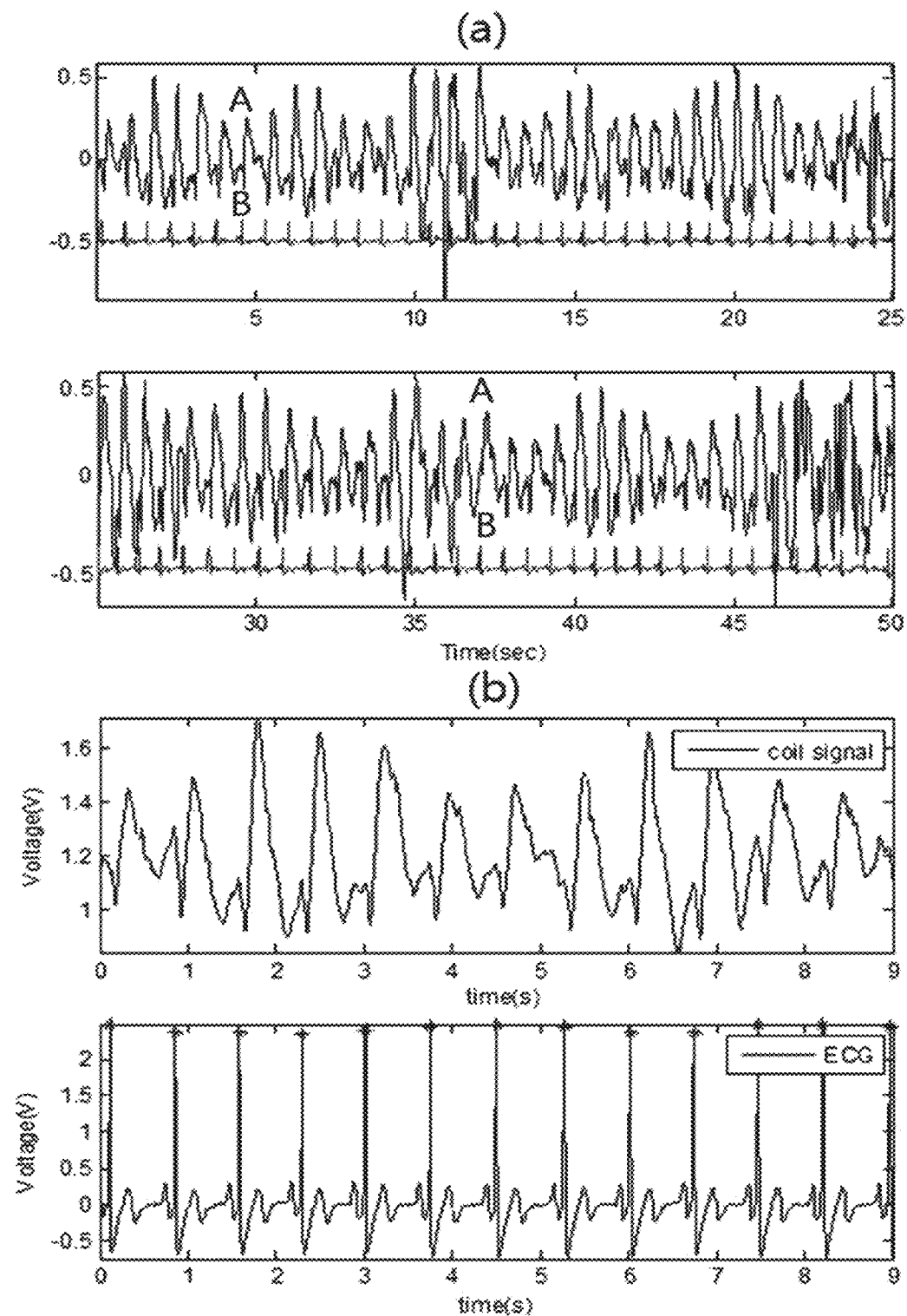
FIG. 22 shows an example of a heartbeat signal detected by the conductive textile-based inductance-type electrode apparatus for bio-signal detection which includes the horizontal dual electrode, as an example of horizontal array-type electrode of the present disclosure.

FIG. 22 shows an example of a heartbeat signal detected by the conductive textile-based inductance-type electrode apparatus for bio-signal detection which includes the horizontal dual electrode, as an example of horizontal array-type electrode of the present disclosure.

In Portion (a) of FIG. 22, a heartbeat signal (A) is detected by the textile electrode (see FIG. 20) where two circular spiral coils are mounted to the electrode-mounted textile sheet 110 to be spaced apart from each other, and an electrocardiogram (ECG) signal (B) is detected as a reference signal by means of an existing electrocardiogram (ECG) detection method in order to check whether the heartbeat signal (A) is normally detected.

Portion (b) of FIG. 22 shows the heartbeat signal and the electrocardiogram (ECG) corresponding thereto, depicted in Portion (a) of FIG. 22, in a partially amplified and enlarged state. An upper graph of Portion (b) of FIG. 22 represents a heartbeat signal, and a lower graph represents an electrocardiogram (ECG) signal. From this, it can be found that a peak of the heartbeat signal is detected by synchronization with an R point (marked by '*') of the electrocardiogram (ECG) signal.

Figure 23:
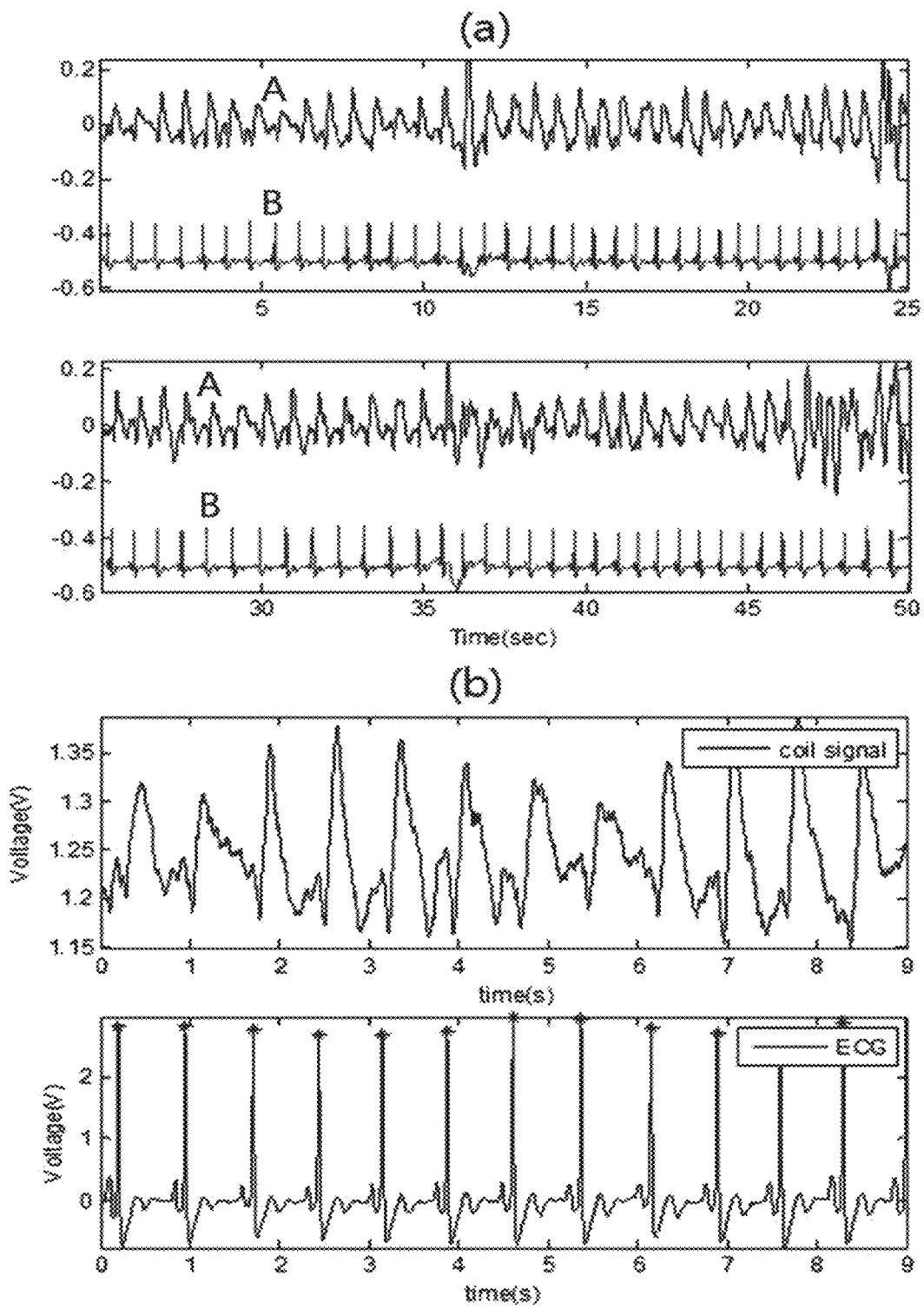
FIG. 23 shows an example of a heartbeat signal detected by the conductive textile-based inductance-type electrode apparatus for bio-signal detection which includes the vertical dual electrode, as an example of vertical array-type electrode of the present disclosure.

FIG. 23 shows an example of a heartbeat signal detected by the conductive textile-based inductance-type electrode apparatus for bio-signal detection which includes the vertical dual electrode, as an example of vertical array-type electrode of the present disclosure.

In Portion (a) of FIG. 23, a heartbeat signal (A) is detected by the vertical dual electrode (see FIG. 19) where textile electrodes having circular spiral coils are mounted to upper and lower portions with an insulating member being interposed between them, and an electrocardiogram (ECG) signal (B) is detected as a reference signal by means of an existing electrocardiogram (ECG) detection method in order to check whether the heartbeat signal (A) is normally detected.

Portion (b) of FIG. 23 shows the heartbeat signal and the electrocardiogram (ECG) corresponding thereto, depicted in Portion (a) of FIG. 23, in a partially amplified and enlarged state. An upper graph of Portion (b) of FIG. 23 represents a heartbeat signal, and a lower graph represents an electrocardiogram (ECG) signal. From this, it can be found that a peak of the heartbeat signal is detected by synchronization with an R point (marked by of the electrocardiogram (ECG) signal.

Figure 24:
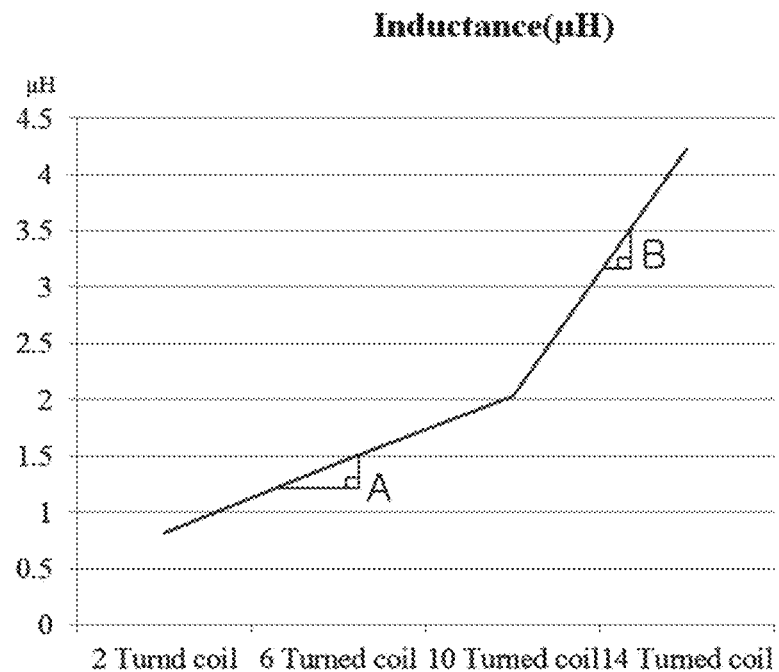
FIG. 24 is a graph showing a magnitude of inductance with respect to a turn number of a spiral coil of the present disclosure.
Figure 25:
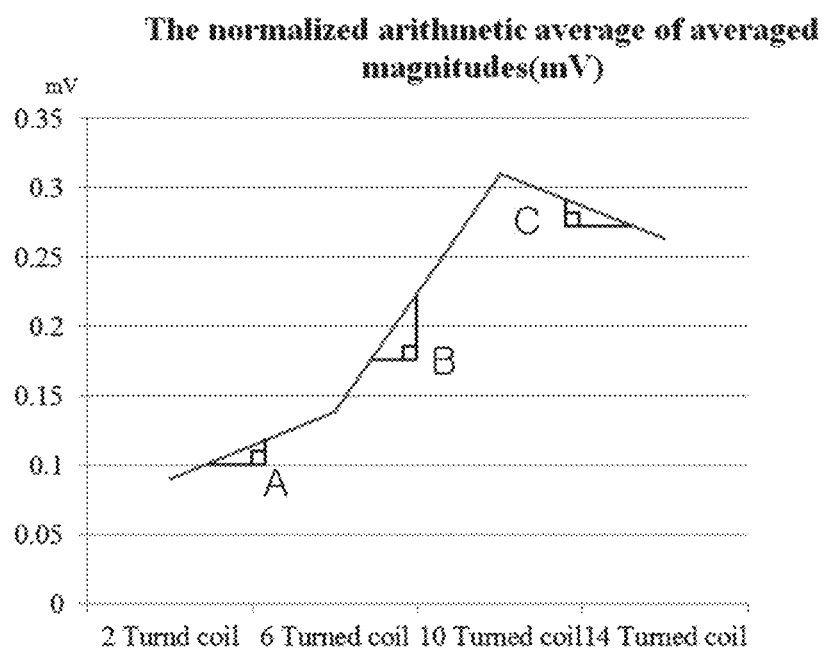
FIG. 25 is a graph showing a magnitude of a heartbeat signal with respect to a turn number of a spiral coil of the present disclosure.

FIG. 24 is a graph showing a magnitude of inductance with respect to a turn number of a spiral coil of the present disclosure, and FIG. 25 is a graph showing a magnitude of a heartbeat signal with respect to a turn number of a spiral coil of the present disclosure.

FIGS. 24 and 25 show an influence given to heartbeat sensing by a turn number of a spiral coil which forms a textile electrode. Here, a relation between the turn number of a spiral coil and the heartbeat sensing has been checked by measuring magnitudes of inductance and heartbeat signal by using four spiral coils with a turn number of 2, 6, 10 and 14. At this time, an interval between coil threads of each spiral coil is the same.

As shown in FIG. 24, the magnitude of inductance is proportional to the turn number of the spiral coil. In detail, regarding a change of the magnitude of inductance, the magnitude of inductance increases with a constant slope (A) until the turn number becomes 10, and then after the turn number exceeds 10, the magnitude of inductance increases with a steeper slope (B) which is about double in comparison to a previous state.

As shown in FIG. 25, the magnitude of heartbeat signal increases until the turn number of the spiral coil reaches a predetermined number, but decreases after that. In detail, the magnitude of heartbeat signal increases with a constant slope (A) until the turn number of the spiral coil becomes 6, but if the turn number exceeds 6 and is smaller than 14, the magnitude of heartbeat signal increases with a steeper slope (B). However, if the turn number of the spiral coil exceeds 14, the magnitude of heartbeat signals changes less.

In conclusion, the magnitude of inductance of a spiral coil which forms the textile electrode is not proportion to the magnitude of heartbeat signal. This is because the curvature of a human body gives an influence. From the experiment results, a bio signal may be measured accurately when the turn number of the spiral coil is 8 to 12, but the present disclosure is not limited thereto.

Even though the present disclosure has been described mainly based on a heartbeat signal in FIGS. 21 to 25, the present disclosure is not limited thereto, and an electrode of the present disclosure may detect all kinds of bio signals, which are detectable by an electrode of the present disclosure, for example an electrocardiogram (ECG) signal, a breath signal, an electromyogram signal or the like.

Though the present disclosure has been described with the limited embodiments and drawings, the present disclosure is not limited to these embodiments, and various changes and modifications can be made thereto from the disclosure by those having ordinary skill in the art. Therefore, the scope of the present disclosure should be defined based on the appended claims, and its modifications and equivalents should also be regarded as falling into the scope of the present disclosure.

| Reference Symbols | |
| --- | --- |
| 10: electrode unit | 101: spiral coil |
| 103: textile sheet | 110: electrode-mounted textile sheet |
| 120: bottom textile sheet | 140: first buffering member |
| 130: second buffering member | 145: buffering member |
| 145a: sub member | 150: connector unit |
| 160: textile electrode coupling unit | 170: detector coupling unit |
| 190: anti-contact unit | 200: textile electrode |
| 250: insulating member | 270: sewing |
| 300: signal detection module | 310: electrode driving unit |
| 320: signal processing unit | 330: transmitting unit |

What is claimed is:

1. A conductive textile-based inductance-type electrode apparatus for bio-signal detection, comprising:
    an electrode unit having at least one textile electrode for receiving an oscillation signal from an oscillating unit and sensing a bio signal of a person, the at least one textile electrode having a spiral coil disposed on a textile sheet and forming a plurality of loops by spirally turning a conductive thread from first end to second end disposed at a center portion thereof;
    a bottom textile sheet configured to contact a skin of the person; and
    a plurality of buffering members disposed between the electrode unit and the bottom textile sheet configured to separate the electrode unit from the skin,
    wherein the plurality of buffering members are spaced apart from each other.

2. The conductive textile-based inductance-type electrode apparatus for bio-signal detection according to claim 1,
    wherein the electrode unit further includes an anti-contact unit disposed between the plurality of loops to prevent the plurality of loops from contacting each other.

3. The conductive textile-based inductance-type electrode apparatus for bio-signal detection according to claim 2,
    wherein the anti-contact unit is formed by one of coating the conductive thread with an insulation material, stitching the textile sheet with an insulating thread, and embossing, printing or adhering a material with insulation to spaces between the plurality of loops.

4. The conductive textile-based inductance-type electrode apparatus for bio-signal detection according to claim 1,
    wherein the conductive thread is formed by one of embroidering, weaving or knitting a conductive yarn, adhering a conductive material to the textile sheet, and printing a conductive material to the textile sheet.

5. The conductive textile-based inductance-type electrode apparatus for bio-signal detection according to claim 1, further comprising:
    a connector unit for electrically connecting the first end and the second end of the spiral coil to the oscillating unit or a signal processing unit so that the bio signal is received by the signal processing unit.

6. The conductive textile-based inductance-type electrode apparatus for bio-signal detection according to claim 5, wherein the connector unit includes:
   a textile electrode coupling unit disposed on the textile electrode; and
   a detector coupling unit disposed on the oscillating unit or the signal processing unit and coupled to the textile electrode coupling unit.

7. The conductive textile-based inductance-type electrode apparatus for bio-signal detection according to claim 6,
   wherein the connector unit is conductive and formed with at least one of a snap button, a buckle, a button, a clip, a hook, a Velcro, a zipper, a cord and a stitch, so that the electrode unit is detachably connected to the oscillating unit or the signal processing unit.

8. The conductive textile-based inductance-type electrode apparatus for bio-signal detection according to claim 1,
   wherein the at least one textile electrode comprises a plurality of textile electrodes and are laminated on the textile sheet.

9. The conductive textile-based inductance-type electrode apparatus for bio-signal detection according to claim 8,
   wherein an insulating member is disposed between the plurality of textile electrodes.

10. The conductive textile-based inductance-type electrode apparatus for bio-signal detection according to claim 1,
    wherein the at least one textile electrodes comprises a plurality of textile electrodes and are disposed on the textile sheet and spaced from each other, and
    wherein the plurality of buffering members are disposed between the plurality of textile electrodes and the textile sheet.

11. The conductive textile-based inductance-type electrode apparatus for bio-signal detection according to claim 10,
    wherein the plurality of textile electrodes are laminated on the textile sheet.

12. The conductive textile-based inductance-type electrode apparatus for bio-signal detection according to claim 11,
    wherein an insulating member is disposed between the plurality of textile electrodes.

13. The conductive textile-based inductance-type electrode apparatus for bio-signal detection according to claim 1,
    wherein the at least one textile electrode is configured to sense one of a heartbeat, an electrocardiogram (ECG), a breath, an electromyogram, a brainwave and a body composition of the person.

* * * * *